United States Patent
Ernst et al.

(10) Patent No.: US 10,518,101 B2
(45) Date of Patent: Dec. 31, 2019

(54) APPARATUS AND METHOD FOR THE PROPHYLAXIS OF HEARING IMPAIRMENT OR VERTIGO

(71) Applicants: Arneborg Ernst, Berlin (DE); Dietmar Basta, Brieselang (DE)

(72) Inventors: Arneborg Ernst, Berlin (DE); Dietmar Basta, Brieselang (DE)

(*) Notice: Subject to any disclaimer, the term of this patent is extended or adjusted under 35 U.S.C. 154(b) by 429 days.

(21) Appl. No.: 15/314,102

(22) PCT Filed: May 27, 2015

(86) PCT No.: PCT/EP2015/061747
§ 371 (c)(1),
(2) Date: Jun. 13, 2017

(87) PCT Pub. No.: WO2015/181251
PCT Pub. Date: Dec. 3, 2015

(65) Prior Publication Data
US 2017/0274219 A1    Sep. 28, 2017

(30) Foreign Application Priority Data

May 27, 2014 (DE) .......................... 10 2014 107 447
May 27, 2014 (DE) .......................... 10 2014 107 448

(51) Int. Cl.
| | | |
|---|---|---|
| *A61N 5/06* | (2006.01) | |
| *H04R 25/00* | (2006.01) | |
| *A61N 1/36* | (2006.01) | |
| *A61N 5/067* | (2006.01) | |

(52) U.S. Cl.
CPC ....... *A61N 5/0603* (2013.01); *A61N 1/36036* (2017.08); *A61N 5/0622* (2013.01);
(Continued)

(58) Field of Classification Search
CPC ............. A61N 5/0603; A61N 1/36036; A61N 5/0622; A61N 2005/0626; A61N 2005/063; A61N 2005/0665; A61N 2005/0627; A61N 2005/067; A61N 2005/0662; A61N 2005/0659; A61N 2005/0651; A61N 2005/0605; H04R 25/604;
(Continued)

(56) References Cited

U.S. PATENT DOCUMENTS

| | | | |
|---|---|---|---|
| 6,157,861 A | 12/2000 | Faltys et al. | |
| 8,012,189 B1* | 9/2011 | Webb ................... | A61N 5/0603 607/88 |

(Continued)

FOREIGN PATENT DOCUMENTS

| | | |
|---|---|---|
| DE | 29720442 U1 | 1/1998 |
| DE | 29808193 U1 | 8/1998 |

(Continued)

*Primary Examiner* — Mark Bockelman
(74) *Attorney, Agent, or Firm* — Agris & von Natzmer LLP; Joyce von Natzmer

(57) ABSTRACT

The invention relates to an irradiation apparatus for the prophylaxis of hearing impairment and/or vertigo, to a system of functionally connected apparatus components which interact with each other, and a method that uses the irradiation apparatus for the prophylactic irradiation of the inner ear with photons in order to prevent hearing impairment and/or vertigo in a wearer of the irradiation apparatus.

40 Claims, 6 Drawing Sheets

(52) U.S. Cl.
CPC ...... *H04R 25/604* (2013.01); *A61N 2005/063* (2013.01); *A61N 2005/0605* (2013.01); *A61N 2005/067* (2013.01); *A61N 2005/0626* (2013.01); *A61N 2005/0627* (2013.01); *A61N 2005/0651* (2013.01); *A61N 2005/0659* (2013.01); *A61N 2005/0662* (2013.01); *A61N 2005/0665* (2013.01); *H04R 25/00* (2013.01); *H04R 2225/021* (2013.01); *H04R 2225/025* (2013.01); *H04R 2225/67* (2013.01)

(58) Field of Classification Search
CPC ........ H04R 2225/021; H04R 2225/025; H04R 2225/67; H04R 25/00
See application file for complete search history.

(56) References Cited

U.S. PATENT DOCUMENTS

| | | |
|---|---|---|
| 8,920,344 B2 | 12/2014 | Ernst et al. |
| 2010/0174329 A1 | 7/2010 | Dadd et al. |
| 2011/0282417 A1 | 11/2011 | Moser et al. |
| 2011/0295331 A1 | 12/2011 | Wells et al. |
| 2013/0023962 A1 | 1/2013 | Stafford et al. |
| 2013/0172960 A1 | 7/2013 | Ahn et al. |

FOREIGN PATENT DOCUMENTS

| | | |
|---|---|---|
| DE | 69728173 T2 | 2/2005 |
| WO | 2007115565 A2 | 10/2007 |

* cited by examiner

APPARATUS AND METHOD FOR THE PROPHYLAXIS OF HEARING IMPAIRMENT OR VERTIGO

CROSS-REFERENCE TO RELATED APPLICATIONS

This is the U.S. national stage of International application PCT/EP2015/061747, filed May 27, 2015 designating the United States and claiming priority to German patent applications DE 102014107448,3, filed May 27, 2014 and DE 102014107447.5, also filed May 27, 2014.

The invention relates to an irradiation apparatus for the prophylaxis of hearing impairment and/or vertigo, a system of operatively connected apparatus components that interact with one another, and methods using the irradiation apparatus for the prophylactic irradiation of the inner ear with photons in order to prevent hearing impairment and/or vertigo in a wearer of the irradiation apparatus.

Hearing represents an important sense for humans for perceiving their environment, and is necessary for oral communication with other humans. As the result of various sources of sound and noise in its surroundings, the human ear is exposed to severe stress that manifests as damage to the cochlea in the inner ear. In addition to the cochlea, the inner ear comprises the vestibular system, which is a key component of the equilibrium organ in humans. The sense of equilibrium is used for determining posture and orientation in space, and is therefore essential for stable posture and movement. A decrease in the sensory hair cells in the cochlea and vestibular system as well as downstream neurons is known as a neuroanatomical sign of degenerative development in the auditory and equilibrium systems due to environmental influences, diseases, or aging processes. The peripheral auditory and vestibular structures in the inner ear, i.e., the receptive and neuronal structures used for hearing and perception of the sense of equilibrium, are affected early on. Initially, the outer sensory hair cells and the spiral ganglion cells die. As development progresses, internal sensory hair cells and central nervous system auditory and vestibular structures are damaged.

Methods for treating hearing impairment exist in the prior art. Prell, et al., *Hear Res.* 226 (1-2): 22-43 (2007) describe the treatment of noise trauma by administration of antioxidants. However, taking an active substance may be associated with side effects.

DE 29720442 U1 and DE 29808193 U1 each describe an apparatus in which a laser is integrated into the earpiece of a sound transmission device or a hearing protection device, the radiation of the laser being intended to prevent damage to the inner ear. However, these prophylactic methods are restricted to situations in which the acoustic perception of the surroundings is limited, and therefore they are not suitable for long-term prophylaxis over an entire day. In addition, the preferred parameter ranges for the laser radiation output are specified at 1 mW to 50 mW and a wavelength of 600 nm to 900 nm. No effective prophylaxis is achieved when the apparatus is used with a general selection of parameters from these ranges.

US 2013/0172960 A1 discloses a method for partial hearing loss reversal using low-level laser therapy (LLLT) following noise trauma. In this method, the inner ear is preferably irradiated daily for a period of 60 minutes with laser light having a wavelength of 780 nm, 830 nm, or 980 nm and an output intensity of 165 mW/cm$^2$. The method defines preferred parameters for treatment following noise trauma, and achieves therapeutic success in particular after more than 10 days of treatment. However, the disclosed method is not suitable for prophylaxis of hearing impairment.

The object of the invention is to provide an apparatus, a system comprising this apparatus, and a method that achieve effective prophylaxis of hearing impairment and/or vertigo and eliminate the disadvantages of the prior art.

This object is achieved by a photon irradiation apparatus according to Claim 1. The irradiation apparatus for the prophylaxis of hearing impairment and/or vertigo is characterized in that the apparatus comprises a photon emitter for irradiating the inner ear, and a computer-controlled control unit that controls the output power of the photon beam based on measuring data.

The apparatus according to the invention may advantageously be incorporated into an apparatus system that comprises a plurality of apparatus components, wherein signals concerning a wearer of the irradiation apparatus and/or the surroundings of the wearer are measured, and in addition an output power (P) of a photon emitter for protective irradiation of the inner ear is computed based on these measuring data, and the output power of the photon emitter is set to the computed value P and the inner ear is irradiated with the output power P. That is, in the system according to the invention, which system relates to a group of interconnected or operatively connected apparatus elements, a plurality of apparatus components interact functionally with one another in order to achieve the objective according to the invention.

A method for the prophylaxis of hearing impairment and/or vertigo, using the irradiation apparatus according to the invention, is disclosed in the independent claims. Preferred embodiments are the subject matter of the dependent claims.

According to Claim 1, the irradiation apparatus for the prophylaxis of hearing impairment and/or vertigo is characterized in that the apparatus comprises a photon emitter for irradiating the inner ear, and an automated, measuring data-based control unit for controlling the output power of the photon emitter.

A photon emitter is preferably understood to mean a radiation source that emits photons. Very preferred embodiments of such photon emitters are photon-emitting lasers or light emitting diodes.

The output power of the photon emitter is understood in particular to mean the total radiation power of the photon beam emitted by the photon emitter. In particular, therefore, the output power of the photon emitter is understood to mean the emitted photon beam energy per unit time. The preferred unit for the output power of the photon emitter is the watt (W) or mW. It is known by those skilled in the art how the output power of a photon beam may be determined, preferably by means of a photometer. In the focusing of the photon beam on a given target, preferably the inner ear, the output power of the photon emitter is understood in particular to mean the radiation power that is incident on the target to be irradiated, in particular the inner ear. This also applies in particular when photons are absorbed by optical elements on the optical path of the photon beam within the photon emitter, as well as by optical elements, for example for conducting the photon beam, outside the photon emitter. The output power of the photon emitter is preferably understood to mean the radiation power that is biologically relevant, i.e., in particular the radiation power that is incident on biological tissue, preferably the inner ear. Furthermore, the power of the photon beam, the photon beam power, and the beam power are preferably understood to mean the output power of the photon emitter. In embodiments in which the photon emitter is limited to a certain wavelength range, the output power of the photon emitter is preferably understood to mean the radiation power integrated over this wavelength range. In addition, increased or decreased photon beam power, increased or decreased irradiation, increased or decreased photon irradiation, and analogous wordings are understood to mean photon irradiation with an increased or decreased output power of the photon emitter. The photon beam intensity, the irradiation intensity, and the intensity of the photon irradiation are expressed in particular by the output power of the photon emitter divided by the cross-sectional area of the photon beam, in particular the cross-sectional area of the photon beam with which the photon beam is incident on biological tissue during the irradiation of the inner ear. The preferred unit of the photon beam intensity is $mW/cm^2$.

An automated, measuring data-based control unit for controlling the output power of the photon emitter is preferably understood to mean an apparatus that controls the output power of the photon emitter based on measuring data concerning, for example, the ambient noise level, the reproducibility of evoked otoacoustic emissions, or the change in bodily positions of the wearer. In particular, the automated, measuring data-based control unit controls the output power of the photon emitter to a value that has been computed by the control unit based on the measuring data. Measuring data are understood in particular to mean data or information that may be recorded by measuring devices, for example microphones or gyrometers. The measuring data particularly preferably relate to information concerning the surroundings of the wearer of the irradiation apparatus, for example concerning acoustic signals, ambient noise, or the sound pressure level in the surroundings. In addition, the measuring data preferably relate to information concerning the wearer him/herself, for example concerning the hearing of the wearer or body sway of the wearer. The measuring data particularly preferably relate to that information that provides an indication of the state of the inner ear of the wearer of the irradiation apparatus, or concerning factors that influence the state of the inner ear of the wearer. Furthermore, the power of the photon emitter is preferably controlled in an automated manner, i.e., preferably without input by the wearer of the irradiation apparatus, in particular preferably without manual input by the wearer by actuation of a rotary knob, a control slide, or other devices for manually controlling the output power of the photon emitter. An automated, measuring data-based control unit is preferably also understood to mean an apparatus not only to which the measuring data may be transmitted, but also on which the measuring data may be processed. The automated, measuring data-based control unit for controlling the output power of the photon emitter therefore preferably comprises a device for recording, processing, and transmitting data, in particular measuring data. The automated, measuring data-based control unit thus preferably comprises an electronic circuit, a computer chip, or some other data processing device. According to the invention, a computer-controlled control unit, a controller, a measuring data-based control unit, or an automated control unit is preferably understood to mean an automated, measuring data-based control unit for controlling the output power of the photon emitter.

The automated, measuring data-based control unit for controlling the output power of the photon beam advantageously allows optimization of the photon irradiation of the inner ear in order to increase the prophylactic effect of the irradiation apparatus. The automated, measuring data-based control unit controls the output power of the photon emitter for irradiating the inner ear based on signals concerning the wearer of the irradiation apparatus and/or the wearer's surroundings. The measuring data-based control of the power of the photon irradiation of the inner ear thus allows in particular an adaptation of the irradiation power to the state of the auditory and/or vestibular structures of the inner ear of the wearer of the irradiation apparatus, and to environmental factors that affect the state of the inner ear. The measuring data-based control of the photon radiation thus allows surprisingly effective prophylactic photon irradiation for preventing damage to hearing and/or equilibrium.

The protective effect of the photon irradiation on the inner ear is understood in particular to mean that the photon irradiation of the inner ear results in an increase in the protective function of the inner ear. The protective effect thus results in particular in protection of the inner ear from potential damage. The protective effect in particular also begins simultaneously with the photon irradiation, which means that the protective effect even increases the protection of the inner ear for stresses that the inner ear experiences during the photon irradiation. However, the protective effect of the photon irradiation on the inner ear particularly preferably persists over an extended period of time, which in particular may be at least one month. The protective effect thus results in a build-up of protection of the inner ear, in particular the auditory and vestibular structures of the inner ear, comprising sensory hair cells, spiral ganglion cells, and neurons, which protection is maintained over an extended period of time, in particular at least one month. Due to this increased protection, a stress on the inner ear results in little or no degenerative development of the auditory and/or vestibular structures. In particular, the protective effect of the photon irradiation is not the same as a therapeutic effect of photon irradiation, which reverses existing hearing impairment or vertigo. Thus, it is preferably not provided that the irradiation of the inner ear takes place significantly after the damage event (for example, one day later). In particular, for therapeutic treatment of hearing impairment the photon beam power would have to be set differently than is the case for prophylactic photon irradiation. According to the invention, the power of the irradiation apparatus is preferably optimized for a high protective effect, and thus for prophylactic photon irradiation.

Prophylactic photon irradiation is preferably understood to mean that the photon irradiation takes place in order to prevent hearing impairment and/or vertigo. The prophylactic photon irradiation is preferably carried out prior to or concurrently with potential damage to the sense of hearing and/or equilibrium. In particular, the prophylactic photon irradiation preferably does not involve therapeutic photon irradiation for treatment of damage to hearing or equilibrium after such has occurred. Prophylactic photon irradiation is preferably based on the discovered, better understood protective effect of photon irradiation. Since the point in time of potential damage to the sense of hearing and/or equilibrium is often not foreseeable, the prophylactic photon irradiation preferably takes place for extended periods over the entire day. Continuous prophylactic photon irradiation intensifies in particular the protective function of the auditory and/or vestibular structures. Since the protective effect of the photon irradiation persists for an extended period of time even after the irradiation, in particular damage to the inner ear that is not foreseeable may be prevented by prophylactic photon irradiation over the entire day. As a result of the prophylactic photon irradiation, degenerative development of the sense of hearing and/or equilibrium may thus preferably be prevented over the long term. The prophylactic photon irradiation therefore preferably does not relate to therapeutic treatment of damage to hearing or equilibrium with the objective of reversal.

The state of the inner ear is preferably understood to mean the state of the auditory or vestibular structures of the inner ear, comprising sensory hair cells, spiral ganglion cells, and neurons. The state of the inner ear is understood in particular to mean the functionality of the inner ear for the sense of equilibrium and for the sense of hearing. A satisfactory state of the inner ear thus indicates in particular a high level of functionality of the inner ear, i.e., in particular good hearing and a good sense of equilibrium. Poor or impaired hearing, such as with hearing disorders and tinnitus, indicates in particular a poor state of the inner ear. Likewise, a decreased sense of equilibrium, for example in the case of frequent dizziness, indicates a poor state of the inner ear. Biologically, the state of the inner ear depends in particular on the state of the auditory or vestibular structures of the inner ear, comprising sensory hair cells, spiral ganglion cells, and neurons. A reduction in the functionality of auditory and vestibular structures of the inner ear, in particular a reduction in the functionality of sensory hair cells or a reduction in the number of sensory hair cells, thus indicates a deterioration of the state of the inner ear.

Factors that influence the state of the inner ear are understood in particular to mean external and internal factors that affect the inner ear. In particular, such factors are understood to mean those that affect the auditory or vestibular structures of the inner ear, comprising sensory hair cells, spiral ganglion cells, and neurons. In particular, such factors are understood to mean those that may impair the state of the inner ear, i.e., that may damage the inner ear, in particular the auditory and vestibular structures of the inner ear. A high noise exposure level due to an increased ambient noise level is in particular an external factor that damages the inner ear. Internal factors that may damage the inner ear are in particular diseases that impair the functionality of the sensory hair cells or that may result in sensory hair cells dying. These include in particular vertebrobasilar circulatory disorders, cardiovascular diseases, arteriosclerosis, metabolic disorders, autoimmune diseases, anemia, inflammatory diseases, and diabetes mellitus.

Photon irradiation of the inner ear in the cells of the inner ear, in particular the sensory hair cells, advantageously brings about certain photochemical reactions that have a protective effect on the cells, in particular when the photon emitter for irradiating the inner ear comprises an automated, measuring data-based control unit for controlling the output power of the photon emitter. These photochemical reactions are also referred to as biostimulation, photostimulation, and photobiostimulation. The finding that the photochemical reactions described below have a particularly great protective effect on cells irradiated according to the invention was novel and surprising. The incident light photons are absorbed in particular by the chromophores in the cells of the irradiated tissue, in particular of the inner ear. Due to the absorption process, electrons of the chromophore are excited and jump from a low-energy orbital into a higher-energy orbital. The energy thus obtained is utilized by the biological system for carrying out numerous different cellular functions. In particular, chromophores in the mitochondria are excited in such a way by the photostimulation. The irradiation of tissue with photons according to the invention thus results in a surprising increase in mitochondrial products, for example adenosine triphosphate (ATP), NADH (the reduced form of nicotinamide adenine dinucleotide (NAD)), proteins, and ribonucleic acid (RNA), as well as a reciprocal increase in oxygen consumption. Cellular respiration is advantageously increased when mitochondria are stimulated by irradiation with photons according to the invention. Due to optimization of the action spectra for the photoinduced biological activity on the absorption spectra of four membrane-bound complexes in the mitochondria, it has been possible to identify the chromophore that plays a key role in the photostimulation according to the invention. This method identified the complex IV, also referred to as cytochrome c oxidase (CCO), as a key chromophore for the protective effect of the photon irradiation.

CCO is a large transmembrane protein complex that contains two copper centers and two heme iron centers as components of the respiratory chain. In the electron transport chain of respiration, high-energy electrons are transported by electron carriers to a series of transmembrane complexes (including CCO), and ultimately to electron acceptors. A proton gradient is thus created which is utilized to produce ATP. The irradiation by photons directly influences ATP production due to the excitation of a transmembrane complex in the electron transport chain. The photon irradiation according to the invention advantageously results in an increase in the production of ATP. In addition, in particular nitric oxide (NO) is released in the cells that are irradiated with photons according to the invention. This observation indicates that CCO and the release of nitric oxide are associated with one another in at least two possible ways. First, the photostimulation according to the invention may result in photoinduced dissociation of nitric oxide. Cellular respiration is down-regulated by the production of nitric oxide by mitochondrial nitric oxide synthases (mt-NOS, a mitochondria-specific isoform of NOS), in that nitric oxide binds to CCO and inhibits it. Due to the binding to CCO, nitric oxide displaces oxygen and thus inhibits cellular respiration and production of ATP. In contrast, the photon irradiation or photostimulation dissociates nitric oxide from CCO, thus resulting in increased ATP production. Second, an alternative mechanism may result in a release of nitric oxide due to photon irradiation. CCO may function enzymatically as a nitrite reductase, reducing nitrite to nitric oxide. This occurs in particular when the oxygen partial pressure is low. The concentration of nitric oxide may thus be increased due to photoinduced excitation of the function of CCO as nitrite reductase. In particular, studies have shown that photon irradiation increases CCO/NO synthesis at physiological nitrite concentrations under ischemic conditions. In addition, in particular the effect of the photon irradiation according to the invention on the electron transport chain is not limited to ATP production of the cells. In particular, the photon radiation according to the invention is understood to mean the radiation whose radiation power is regulated, based on measuring data, by controlling the output power of the photon emitter. It was unexpected that in particular this controlled photon radiation allows surprisingly good achievement of the object according to the invention primarily via the above-mentioned increase in mitochondrial products, in particular in wearers or persons who could not be helped by apparatuses of the prior art with regard to the prophylaxis of hearing impairment and vertigo. It was very surprising that both hearing damage and vertigo could be prevented in this way. Oxygen acts as an electron acceptor in the electron transport chain, and in this process is converted to water. A portion of the metabolized oxygen hereby generates reactive oxygen species (ROS) as a natural by-product. ROS are chemically active molecules that play an important role in cellular signal cascades, regulation of the cell cycle, activation of enzymes, and synthesis of nucleic acid and proteins. Since the photon irradiation results in increased oxygen, it also brings about an increase in the production of ROS. The ROS also activate transcription factors for the expression of various stimulating and protective genes. These stimulating and protective genes regulate in particular cellular proliferation and migration as well as the production of cytokines and growth factors. The photon irradiation according to the invention advantageously stimulates these processes. In addition, ROS are part of the cellular mechanisms that result in the death of, or in the deterioration of the state of, the sensory hair cells of the inner ear. This is the case in particular when noise results in damage to auditory and/or vestibular structures. It has surprisingly been found that the protective effect of the photon irradiation preferably has a strong two-phase dependency on the irradiation power and/or irradiation period. If the irradiation takes place with a power that is too low, or over too short a time period, this results in only limited photostimulation. On the other hand, if the inner ear is irradiated with a power that is too high, or if the irradiation takes place over too long a time period, the effective photostimulation of the cells is inhibited, and negative side effects may additionally inhibit a protective effect of the photon irradiation. The described two-phase dependency on the irradiation power and/or irradiation period justifies the need for regulating the irradiation power and/or irradiation period as a function of external and/or internal influences in order to be able to carry out the photon stimulation in the optimal dosage range for the protective effect. In particular, it has been recognized according to the invention that the magnitude of the photon beam power for an optimal protective effect depends on the state of the inner ear of the wearer and even on factors that influence the state of the inner ear. For example, it has been determined that in the case of stress on the inner ear due to noise, cellular processes are triggered that counteract the functional mechanism of the protective effect. Thus, for example, cellular ATP production is lowered due to stress on the sensory hair cells from acoustic irradiation. This effect may surprisingly be compensated for, and an optimal protective effect achieved, by a preferred increase in the photon irradiation, in particular by the controlled photon radiation during the acoustic irradiation. In addition, the ability to excite the electron transport chain, in particular the transmembrane complex cytochrome c oxidase, by photon irradiation is decreased in sensory hair cells having a low functionality. It was totally unexpected that an optimal protective effect could be achieved by increasing the photon beam power during the irradiation of sensory hair cells having reduced functionality. This results in particular in a new clinical situation. Preventive irradiation is also made possible for patients who already have hearing impairment or vertigo, in particular diseases that are caused by reduced functionality of the sensory hair cells. This concerns in particular patients with hearing disorders, tinnitus, or dizziness. Previously, there were no prophylactic irradiation options for these patients using the means of the prior art.

The irradiation intensity and the irradiation period for an optimal protective effect of the photon irradiation on the auditory and/or vestibular structures of the inner ear may thus advantageously be set according to the invention in particular by the measuring data-based control unit. The measuring data-based control of the power and/or duration of the photon irradiation of the inner ear thus results in surprisingly effective prophylaxis of hearing impairment and/or vertigo, in particular that caused by damage in particular to the sensory hair cells, the spiral ganglion cells, and downstream neurons.

In addition, the measuring data-based adaptation of the power of the photon emitter allows in particular long-term use of the irradiation apparatus on a daily basis, for up to 24 hours a day, as a prophylactic means for hearing impairment and vertigo. This is possible due to the fact that the measuring data-based control of the photon power allows adaptation to the individual needs of the wearer and to changing environmental conditions. The irradiation power may be set by computer control, based on measuring data, for an optimal prophylactic effect in order to avoid hearing impairment and vertigo. Unnecessary stress on the inner ear due to excessively high photon irradiation, which may occur during long-term irradiation of the inner ear within the scope of prophylactic photon irradiation, is thus avoided. In addition, too low an irradiation level of the inner ear, which results in an insufficient prophylactic effect, is avoided.

A preferred use of the irradiation apparatus on a daily basis is thus possible for up to 24 hours a day for multiple days, weeks, or months, whereby the power of the photon emitter may be adapted to the hearing and/or equilibrium of the wearer and to environmental conditions, in particular environmental conditions that may damage the sense of hearing or equilibrium. Use of the irradiation apparatus over a long time period, daily for at least 10 hours a day for multiple days, months, or years, using a photon beam power that is adapted to the wearer and/or the environmental conditions, surprisingly results in a particularly strong increase in the protective effect, which particularly effectively prevents hearing impairment as well as vertigo. The protective effect of the photon irradiation relates in particular to the protection of the sensory hair cells of the inner ear from degenerative development. As a result, the photon irradiation advantageously prevents hearing impairment as well as vertigo. The possibility for individualized adaptation of the power of the photon beam has unexpectedly resulted in a surprising increase in wearing acceptance by wearers of the apparatus. Increased wearing acceptance in turn results in daily use over an extended period, thus increasing the protective effect of the apparatus in practical trials. Furthermore, photon beam power that is adapted in this way optimizes the energy efficiency of the irradiation apparatus and allows longer use of the irradiation apparatus daily for up to 24 hours a day over multiple days. In embodiments in which the irradiation apparatus is operated with a battery, in particular longer operation without changing the batteries is possible. In addition, with the irradiation apparatus the irradiation energy may be optimized with respect to time over the day. In particular, the protective effect of the photon radiation on sensory hair cells of the inner ear is a function of the state of the sensory hair cells as well as external factors that affect the state of the sensory hair cells. Adapting the photon radiation to the state of the sensory hair cells and to factors that influence the state of sensory hair cells allows individualized, long-term prophylaxis of hearing impairment and vertigo. In particular, measuring data-based adaptation of the photon beam power achieves a surprisingly greater protective effect than prophylactic photon irradiation using apparatuses that, for example, irradiate the inner ear with a constant photon beam power.

In particular, the invention further relates to use of the irradiation apparatus according to the invention for providing a means for prophylactic photon irradiation having the mentioned technical features of the apparatus according to the invention. In particular, the prophylactic photon irradiation takes place in an automated manner, so that preferably no medical practitioner is needed for providing the means and/or for carrying out the prophylactic photon irradiation.

In certain embodiments, the invention further relates to an apparatus comprising a photon emitter with controllable and/or regulatable output power for irradiating the inner ear of a wearer of the apparatus in order to prevent damage from hearing impairment and/or vertigo. In particular, the invention further relates to an apparatus comprising a photon emitter with controllable and/or regulatable output power for irradiating the inner ear of a wearer of the apparatus in order to prevent hearing impairment and/or vertigo damage, in combination with a measuring device for measuring acoustic signals, a measuring device for measuring evoked otoacoustic emissions, and/or a measuring device for determining the change in bodily position of the wearer of the apparatus. It was very surprising that these combinations result in particularly good achievement of the object according to the invention. Unexpected success is achieved by the mentioned combinations.

In another preferred embodiment, the irradiation apparatus according to the invention comprises a device for measuring acoustic signals in the surroundings. It is known that an increase in the ambient noise level results in degenerative development of the hearing and equilibrium organ. In particular, an increase in the ambient noise level damages auditory and vestibular structures in the inner ear, comprising sensory hair cells, spiral ganglion cells, and neurons of the ascending auditory pathways. Tests have shown that the protective effect of photon irradiation on these structures is increased when the radiation power is adapted to the stress on the inner ear, i.e., preferably when the photon beam power is increased with increasing stress on the inner ear due to ambient noise. For measuring the ambient noise level, the device for measuring acoustic signals preferably comprises a sound level meter that preferably comprises a measuring microphone, whereby the sound level meter determines the sound pressure level in the surroundings. The measuring data concerning the acoustic signals in the surroundings of the wearer for determining the ambient noise level are preferably transmitted, in the form of parameter values concerning the sound pressure level in the surroundings, to the automated, measuring data-based control unit. Based on the parameter values concerning the sound pressure level, the automated, measuring data-based control unit may adapt the photon irradiation for protecting the inner ear to the stress on the inner ear in a computer-controlled manner in real time. In particular, the photon irradiation may be increased as the ambient noise level rises, in a monotonically increasing manner but not necessarily in a continuously increasing manner. The protective effect of the photon radiation on the inner ear, in particular on the auditory and/or vestibular structures of the inner ear, comprising sensory hair cells, spiral ganglion cells, and neurons, is advantageously particularly great when the irradiation takes place during the stress on the inner ear due to an increased noise level. During the time that the inner ear is exposed to potentially damaging noise irradiation, in particular an increased radiation power of the photon beams is necessary in order to achieve a protective effect and thus prevent potential damage to the inner ear in particular due to noise irradiation. The finding that it is advantageous to increase the photon irradiation when the inner ear is exposed to a noise stress during the photon irradiation was very surprising. One possible explanation is that the acoustic irradiation subjects sensory hair cells to stress, and triggers cellular processes that counteract the functional mechanism of the protective photon irradiation. Simultaneously increasing the photon beam power during the noise exposure may compensate for this effect.

In one preferred embodiment, the noise level that acts on the inner ear due to a sound pressure level is determined in a preferred sound frequency range of 50 Hz to 20,000 Hz, particularly preferably 250 Hz to 8000 Hz. Increased damage to the auditory and vestibular structures of the inner ear occurs as the result of noise irradiation in the range of 50 Hz to 20,000 Hz, in particular 250 Hz to 8000 Hz. Furthermore, experiments have shown that more powerful photon irradiation of the inner ear is advantageous for protecting the inner ear in a particularly effective manner from damage due to severe noise stress when the inner ear is exposed to severe noise stress due to acoustic irradiation in particular in a sound frequency range of 50 Hz to 20,000 Hz, very particularly preferably 250 Hz to 8000 Hz. Increasing the power of the protective photon irradiation when there is an increase in the sound pressure level, measured in the surroundings, in a frequency range of in particular 50 Hz to 20,000 Hz, very particularly preferably 250 Hz to 8000 Hz, results in a particularly high preventive effect. In addition, the sound pressure level is preferably determined using a weighting filter, preferably in dB (A) weighting according to DIN EN 61672-1:2014-07. The dB (A) weighting or equivalent weighting filters reflect(s) particularly well the biological effect of sound on the sensory hair cells of the inner ear, in particular the human inner ear.

Quantifying the ambient noise level in the sound frequency range of 250 Hz to 8000 Hz and determining the sound pressure level in this frequency range in dB (A) weighting thus allows in particular the determination of a biologically relevant parameter that reflects the effect of the sound on the state of the sensory hair cells with a particularly high level of medical relevance. Adjusting the photon radiation thus allows particularly effective adaptation of the photon beam power to the biological acoustic effect on the sensory hair cells and the state of the sensory hair cells. Adapting the photon radiation to the ambient noise level allows individualized prophylactic irradiation of the inner ear, which irradiation is adjusted to the potential for damage by the ambient noise. In addition, in particular acceptance of wearing the device is thus increased, and long-term prophylactic irradiation over the entire day is made possible. This surprisingly results in much more effective prevention of hearing or equilibrium damage compared to prophylactic irradiation whose irradiation power is provided independently of ambient noise.

In one preferred embodiment, the irradiation apparatus comprises a device for measuring evoked otoacoustic emissions of the inner ear. Suitable devices and methods for carrying out such measurements are known to those skilled in the art, and are disclosed, among other sources, in standard literature such as Robinette R. M. (Ed.), Glattke T. (Ed.), *Otoacoustic Emissions—Clinical Applications,* 3rd Edition, New York: Thieme 2007.

Measurements of evoked otoacoustic emissions are based on the principle that structures in the inner ear, in particular the outer sensory hair cells of the inner ear, actively emit acoustic signals. These signals are referred to as otoacoustic emissions. Otoacoustic emissions may occur spontaneously or may be evoked, i.e., induced by acoustic stimuli. The device for measuring evoked otoacoustic emissions of the inner ear therefore preferably comprises a sound generator, preferably a speaker, that is able to generate acoustic signals that are suitable for stimulating the sensory hair cells of the inner ear, and a measuring microphone that is able to record the otoacoustic emissions of the inner ear, and that is therefore preferably able to record an acoustic signal between −5 dB and 5 dB.

Based on the above-mentioned standard literature, among other sources, it is known to those skilled in the art how to determine, from these measuring data, parameters that provide information concerning the state of the inner ear, in particular information that describes the state of the outer sensory hair cells or the number of outer sensory hair cells. One preferred parameter is so-called reproducibility. For determining reproducibility, a plurality of acoustic signals is transmitted to the inner ear, preferably by a sound generator or speaker, and for each of these acoustic signals it is determined, preferably by a measuring microphone, whether an otoacoustic emission has been evoked by the acoustic signal. Reproducibility is equal to the ratio of the number of detected evoked otoacoustic emissions to the number of transmitted acoustic signals. If, for example, a total of 100 acoustic signals are transmitted, and, of these 100 signals, 60 otoacoustic emissions are detected, the reproducibility is 60%. Reproducibility, as a particularly informative parameter, advantageously reflects the functionality of the inner ear for responding to acoustic signals. Reproducibility is therefore a particularly relevant parameter for determining the biological functionality of the inner ear, in particular the state or the number of sensory hair cells.

The irradiation apparatus preferably also comprises a data processing device that automatically computes the above-described parameters based on the measuring data of the evoked otoacoustic emissions. The measuring data of the evoked otoacoustic emissions and/or the parameters that are computed from the measuring data are preferably transmitted to the automated, measuring data-based control unit. The computer-controlled control unit is thus able to adjust the output power of the photon radiation based on, i.e., as a function of, the parameters that have been determined by the measurement of otoacoustic emissions, and that preferably correspond to the state or the number of outer sensory hair cells. The state of the sensory hair cells is preferably understood to mean the capability of the sensory hair cells to respond to acoustic signals, i.e., to relay, for example, acoustic signals for perceptions of an auditory event to neurons, or to generate otoacoustic emissions based on the acoustic signals. Tests have shown that the photon radiation for the prophylaxis of hearing impairment or vertigo acts in particular on the sensory hair cells of the inner ear and achieves a protective effect there. A preferred adaptation of the photon radiation to the state of the sensory hair cells or to the number of sensory hair cells surprisingly allows an increase in the protective effect on the sensory hair cells. In particular, the irradiation of the photon radiation may be increased when there is a reduction in the number of sensory hair cells or a deterioration in the state of the sensory hair cells. Such an adaptation of the power of the photon radiation to the state and/or number of sensory hair cells achieves a surprisingly high level of protection of the inner ear, and thus prevents in particular long-term hearing impairment and vertigo, compared to that possible in the prior art.

In another preferred embodiment, the device for measuring evoked otoacoustic emissions comprises one or more sound generators for generating acoustic signals that stimulate the outer hair cells of the inner ear with respect to otoacoustic emissions, and a measuring microphone for measuring these otoacoustic emissions. In one particularly preferred embodiment, the device is suitable for measuring evoked otoacoustic emissions in order to measure distortion product otoacoustic emissions (DPOAE). Based on the above-mentioned standard literature *Otoacoustic Emissions—Clinical Applications*, among other sources, it is known to those skilled in the art how DPOAE may be measured. In particular, the device may generate two simultaneous sine tones having frequencies f1 and f2, using one or more sound generators, and may measure the distortion product of the otoacoustic emissions at at least one frequency f3, using a measuring microphone. This preferred embodiment, comprising a device for carrying out DPOAE [measurements], is particularly well suited for determining the state and/or the number of sensory hair cells. In particular, it has been shown that the measurements of DPOAE based on the increased frequency specificity are surprisingly and particularly suited for conducting measurements of otoacoustic emissions in environments having a high ambient noise level. In particular, the preferred device for measuring DPOAE thus allows a measurement of the state and/or the number of sensory hair cells of the inner ear in various everyday situations, for example in the living room, at work, at a concert, or when traveling. Adapting the power of the photon radiation to the internal auditory and/or vestibular structures, in particular over the entire day, is possible with little complexity. This particularly good everyday use of the irradiation apparatus results in particularly effective protection of the inner ear from any hearing impairment and/or vertigo.

In another preferred embodiment, the measuring microphone for measuring the otoacoustic emissions is also used for measuring the ambient noise level. In this particularly preferred embodiment, the measuring microphone is thus an integral part of the device for measuring acoustic signals from the surroundings, and also of the device for measuring the otoacoustic emissions. This two-fold utilization of the measuring microphone for determining measuring data improves in particular the level of effort for manufacturing the irradiation apparatus and for operating the irradiation apparatus. In particular, more cost-effective production of the irradiation apparatus is thus possible. In addition, due to the synergistic use of a measuring microphone for different functions, the energy consumption for operating the irradiation apparatus is surprisingly reduced. The individualized adaptation of the photon radiation to the state of the inner ear, made possible by the device for measuring the otoacoustic emissions, also increases in particular wearing acceptance. According to tests, this may be attributed, at least in part, to the fact that a wearer of the apparatus is aware that the irradiation for his/her inner ear is set neither too high, which could possibly lead to undesirable side effects, nor too low, which would not provide an optimal protective effect. Increased wearing acceptance allows long-term use of the prophylactic means over the entire day, and may thus achieve more effective prevention of hearing impairment or vertigo than has been possible in the prior art.

In one preferred variant, the irradiation apparatus comprises a device for measuring the change in a bodily position of the wearer of the irradiation apparatus, the device transmitting measuring data to the control unit for controlling the output power of the photon emitter. By use of such a measuring device, it is preferably possible to adapt the protective photon irradiation to the state of the sense of equilibrium or to factors that influence the state of the sense of equilibrium. In particular, an advantageous protective effect has been determined when the photon irradiation is increased when there is a disturbance in the sense of equilibrium. A disturbance in the sense of equilibrium manifests in persons in particular by an increased change in the bodily position as occurs during swaying or falling, for example. It has been possible to prevent further exacerbation of vertigo in these persons in a particularly effective manner by increasing the power of the photon radiation as a function of the severity of the vertigo. Vertigo is often attributable to a reduced functionality or number of the sensory hair cells in the inner ear, in particular in the vestibule. An increase in the photon radiation in the event of vertigo is therefore adapted to the state and/or the number of sensory hair cells, and thus increases the protective effect on the sensory hair cells. The protective effect is thus increased due to a preferred increase in the photon irradiation as a function of the measured change in the bodily position, in particular a measured reduction in control of the body's center of gravity.

In another preferred embodiment, the device described in the preceding paragraph determines the change in the bodily position of the wearer of the irradiation apparatus in three-dimensional space as the change in the angular velocity of forward, backward, and lateral movements of the body's center of gravity on the wearer. Numerous tests indicate that this type of determination of the change in the bodily position describes in a particularly realistic manner the body sway and/or the bodily movements that increasingly occur when a person's sense of equilibrium is disturbed.

In particular, the change in the angular velocity of forward, backward, and lateral movements of the center of gravity of the wearer's body is used as an informative parameter for distinguishing between voluntary movements and movements caused by vertigo.

In one preferred embodiment, the change in the angular velocity of forward, backward, and lateral movements of the body's center of gravity in three dimensions is determined by a 3-axis gyrometer chip. The 3-axis gyrometer chip preferably comprises three gyrometers situated orthogonally with respect to one another. A particularly preferred 3-axis gyrometer chip is the L3G4200D from STMicroelectronics. Gyrometers are preferably understood to mean devices that are able to measure rotary movements, in particular angular velocities of the rotary movements. Suitable gyrometers are known to those skilled in the art and are commercially available. In particular, gyrometers in the prior art are known that determine the Coriolis force as an inertia force in rotating reference systems. In these gyrometers, changes in capacitance are recorded as a function of the change in the Coriolis force during a movement. Since the Coriolis force is in a fixed relationship with respect to the angular velocity of rotation, the measured changes in capacitance may be converted into numerical values of the angular velocity using a microprocessor. 3-axis gyrometer chips are likewise commercially available. Due to the orthogonal arrangement of three gyrometers in the 3-axis gyrometer chips, the angular velocity of a rotation of the device for measuring the change in a bodily position may be determined in three dimensions, i.e., along three reference axes. The angular velocities determined in this way are preferably represented as so-called displacement vectors in the form a=(x, y, z). In this regard, x, y, and z each denote the values of the angular velocities in degrees per second (°/s) in the particular spatial dimension of the Cartesian coordinate system that is spanned by the reference axes of the gyrometers. The z reference axis preferably corresponds to the body axis of the wearer of the irradiation apparatus, and the z value of the displacement vector preferably denotes up and down movements of the wearer. The angular velocity along the x reference axis, the x value of the displacement vector, preferably describes lateral movements of the wearer, and the angular velocity along the y reference axis, the y value of the displacement vector, preferably describes forward and backward movements of the wearer.

In particular, changes in the bodily position of the wearer of the irradiation apparatus are preferably determined as displacement vectors in the form a=(x, y, z) for each spatial quadrant (see FIG. 5).

In another embodiment, the device for measuring the change in a bodily position comprises two gyrometers arranged orthogonally with respect to one another. These two gyrometers determine the angular velocity in two orthogonal reference axes. The two gyrometers preferably determine the x and y values of the displacement vector a=(x, y, z) defined above. The value of the angular velocity z in the third reference axis, which is orthogonal with respect to the other two axes, is computed in this embodiment. The following mathematical formulas in particular may be applied for the computation:

$$\alpha' = \arccos\frac{(b'^2 + c'^2 - a'^2)}{2b'c'}$$

where $$a' = \frac{b}{\cos\alpha} - b$$

$$b' = \sqrt{c^2 - b^2}$$

$$c'^2 = a'^2 + b'^2 - 2a'b'\cos\gamma'$$

$$c = a' + b$$

$$\gamma' = 180° - 90° - \alpha$$

As illustrated in FIG. 6, the pivot point a corresponds to the angle along the x or y axis. For computing the angle ($\alpha'$) along the z axis using trigonometric functions, this angle is transposed by a distance b. However, this has no effect on the result of the angular computation. In particular, this means that b may assume arbitrary values greater than 0 for the computation without changing the result of the computation of $\alpha'$.

For computing an angular velocity in °/s along the z axis based on known angular velocities in the x and y axes in °/s, the computed angles become, through the joint reference to the time unit of one second, a measure of the movement in the sense of the angular velocity. In particular, for computing an angular velocity along the z axis based on known angular velocities in the x and y axes, the larger value of the angular velocity along the x and y axes is used. In the above formulas, this value of the angular velocity is set equal to the angle $\alpha$ with reference to the time unit (s). The sought magnitude of the value of the angular velocity in the third reference axis along the z axis corresponds to the angle $\alpha'$ with reference to the time unit (s).

One gyrometer may advantageously be spared by computing the angular velocity in the third orthogonal reference axis (z) based on known angular velocities along the x or y axis. That is, only two gyrometers are used in this embodiment instead of three gyrometers as in the 3-axis gyrometer. This results in particular in a more lightweight design of the device for determining the change in the bodily position, and is particularly cost-effective.

One advantage of the device for measuring the change in a bodily position of the wearer of the irradiation apparatus is that the changes in the bodily position at rest and during movement in space may be determined.

In one preferred embodiment, the device for measuring the change in the bodily position is attached at the midsection of the wearer of the irradiation apparatus. In one particularly preferred embodiment, this takes place using a belt that fixes the device for measuring the change in the bodily position in the vicinity of the hip. In other preferred embodiments, the fastening takes place using a rubber band or a textile strap containing rubber fibers. Of course, the fastening to the body may also take place using a leather harness, a textile harness, or a synthetic leather harness.

The measured change in the bodily position advantageously corresponds exactly to the change in position of the center of gravity of the wearer's body when the measuring device is positioned in the vicinity of the hip. In particular, it has been shown that a change in the bodily position determined in this way detects swaying, and possibly falls, very realistically. In addition, due to such positioning of the measuring device, a controlled movement may be distinguished particularly well from an uncontrolled movement, which occurs more frequently with wearers of the apparatus who have vertigo.

In one particularly preferred variant, in the device for measuring the change, standard values for displacement vectors during various activities are additionally stored. The standard values are determining by using the device for measuring the change in the bodily position in a plurality of persons of various age groups who perform the indicated activities. In particular, the standard values correspond to the maximum values of specific displacement vectors in the particular spatial quadrants as illustrated in FIG. 5. The standard values for the maximum displacement vectors a1-a4 for the particular spatial quadrant thus span an ellipse that is determined by the maximum spatial displacement vectors. In particular, using the device on 100 healthy persons (48 females, 52 males), age-specific standard values for the maximum spatial displacement vectors were created for specific movement sequences for each spatial quadrant (a1-a4, see FIG. 5) in the form a=(x, y, z) (see Table 1). As the result of storing standard values for the various activities, including standing up, balancing, walking, or climbing stairs, among others, the device for determining the change in the bodily position has a broad spectrum of reference values.

It is thus advantageously possible to estimate the movement of the wearer of the irradiation apparatus particularly well in a variety of everyday situations. This allows a particularly good estimation of whether the movement corresponds to an intentional movement within the scope of the activity. This is the case in particular when the measured displacement vector is smaller than the stored standard value of the displacement vector in the particular spatial quadrant for the particular activity. An unintentional movement also indicates in particular the loss of equilibrium. Such an unintentional movement is detected in particular by the measured displacement vector exceeding the standard value of the displacement vector in the particular spatial quadrant and for the particular activities and age groups.

In preferred variants, programs that indicate to the device which activity the wearer of the apparatus is performing or intends to perform are selectable on the device for measuring the change in the bodily position. The program may preferably be selected manually or via voice recognition. In addition, the device may also activate the programs automatically, for example by recognizing movement sequences by evaluating brain or muscle activities.

In one particularly preferred embodiment, the measured displacement vectors are transformed nonlinearly in order to determine the change in the bodily position of the wearer of the irradiation apparatus. The basis of this particularly preferred embodiment is the novel finding that the spatial axes have a nonlinear relationship to one another when the body's center of gravity is shifted. In particular, a movement in the x axis or y axis does not correspond to the same extent to an unintentional movement, such as for falling or swaying, as is the case for a movement along the z axis. The measured displacement vectors of the form a=(x, y, z) are therefore preferably transformed in order to determine the movement of the bodily position. The angular velocities in the x, y, and z axes are hereby adapted in order to quantify the change in the body's center of gravity as realistically as possible.

The following compensatory method is preferably applied for this purpose: First, using a newly developed formula, the value f is determined for each spatial quadrant as a function of the x and y values of the spatial displacement vectors a=(x, y, z). If x>y, f is a function of x. f is preferably a function of x of the form $f=ax^2$. If y>x, f is a function of y. For y>x, f is preferably a function of the form $f=ay^2$.

In one very particularly preferred form, the function f takes the following form if the value x of the spatial displacement vector is greater than the value y of the spatial displacement vector; i.e., for x>y, f is:

$$f = \frac{z}{z_{n_{standard}}} 0.0017 \cdot x^{1.9462}$$

If y>x, f is:

$$f = \frac{z}{z_{n_{standard}}} 0.0017 \cdot y^{1.9462}$$

In the formula, z corresponds to the value z of the displacement vector of the spatial quadrant under consideration. The same correspondingly applies for x and y. The z standard value is preferably read from Table 1 for the particular activity (for example, standing in the dark) and the particular age group. The result (f) is subtracted from the value x of the displacement vector of the spatial quadrant under consideration when x>y. The result (f) is subtracted from the value y when x<y. The displacement vectors transformed in this way may also be referred to as effective displacement vectors of the form $a^*=(x^*, y^*, z^*)$, since they reflect particularly well the relevant change in the body's center of gravity of the wearer of the irradiation apparatus. In particular, in the transformed displacement vectors, the angular velocities along the x and y reference axis (the values $x^*$ and $y^*$) are smaller in comparison to the angular velocity along the z axis ($z^*=z$). This reflects particularly well the actual conditions of human movement sequences in space and during swaying or falling due to unintentional movements. By use of this preferred embodiment, the power of the photon irradiation may thus be adapted in a particularly precise manner to the state of the sense of equilibrium of the wearer of the irradiation apparatus.

The device for measuring the change in the bodily position thus preferably determines the change in bodily position as a displacement vector of the form a=(x, y, z), where x, y, z are expressed in °/s. The device for measuring the change in the bodily position particularly preferably determines the change in the bodily position as a displacement vector, transformed using the above method, of the form $a^*=(x^*, y^*, z^*)$, where $x^*$, $y^*$, and $z^*$ are expressed in °/s and the values $x^*$ and $y^*$ are adjusted using the method described in the preceding paragraph.

An unintentional movement is detected in particular by an exceedance of the measured displacement vector, preferably of the displacement vector transformed using the above method, in comparison to the standard value of the maximum displacement vector in the particular spatial quadrant. It has surprisingly been shown that increasing the prophylactic photon irradiation provides a particularly protective effect for detecting these types of unintentional movements. The power of the photon irradiation is advantageously increased in particular as a function of the change in the bodily position exceeding the corresponding standard value. Surprisingly, in particular the sense of equilibrium of the wearer is intensified by increasing the photon irradiation of the inner ear in the event of great changes in the bodily position. It has been shown that prophylactic photon irradiation that is adapted in this way is particularly suitable for preventing vertigo. In addition, in particular an application of the irradiation apparatus for patients with vertigo is possible by integrating the device for measuring the change in bodily position into the irradiation apparatus. This allows a preferred application of the irradiation apparatus for a totally new patient population comprising patients with dizziness caused by high blood pressure, otolith function disorders, neuritis vestibularis, semicircular canal function disorders, Ménière's disease, and various symptoms of dizziness such as rotary vertigo, vestibular vertigo, and up-and-down vertigo.

Previously, it has not been possible to carry out photon irradiation of patients with vertigo using optimally adjusted photon beam power. In particular, some patients complained of an additional dizzy feeling that could be diminished only by reducing the photon beam power. In addition, however, no improvement in the feeling of equilibrium was determined in patients when a low photon beam power was used. As the result of increasing the photon irradiation when the change in the bodily positions exceeds the standard values stored by the maximum displacement vectors in the particular spatial quadrant, body sway surprisingly occurs much less frequently in the affected persons. This has been demonstrated based on measurement of the displacement vectors or the change in the bodily position determined therefrom. These patients no longer complained of an additional dizzy feeling or feeling of being unwell, which indicates that the photon beam power is set in a particularly satisfactory manner by the described adaptation to the measuring data of the device for determining the change in the bodily position.

In one particularly preferred variant, the irradiation apparatus comprises actuators that are attached to the body, wherein the activity of the actuators is proportional to the determined change in a bodily position, and the activation does not occur within limits of the values of the change in a bodily position based on the movement sequence. In this embodiment, the irradiation apparatus preferably comprises actuators or stimulators that, based on the measuring data of the device for determining the change in the bodily position, provide a signal to the wearer of the apparatus. In one particular embodiment of the invention, the intensity of the electrical resistance is advantageously so great that the activity of connected stimulators (actuators) is equal to zero. In contrast, the stimulators (actuators) are activated as soon as the measured or transformed spatial displacement vectors exceed the standard values of the maximum displacement vectors in the particular spatial quadrants. The sense of equilibrium is advantageously trained by the stimulation when the standard values for the displacement vectors are exceeded. In particular, further deterioration of the sense of equilibrium may be effectively prevented by a feedback signal that is provided in this way when swaying or loss of equilibrium occurs.

Furthermore, the integration of actuators into the irradiation apparatus results in a very surprising synergistic effect with regard to the prophylaxis of vertigo. It has been found that, due to the use of actuators with concurrent photon irradiation of the inner ear, the learning success, i.e., the training of the sense of equilibrium, surprisingly has a greater protective effect than would be expected by summing the protective effects from using only actuators or only the photon emitter for irradiating the inner ear. In particular, those structures of the inner ear situated downstream from the sensory hair cells are excited by the stimulation with actuators. In turn, as a result of the increased activity of the inner ear, the photostimulation of the irradiated cells achieves a particularly great protective effect.

Preferred actuators within the meaning of the invention are vibration actuators such as the 6CH-1201-WL-00 balance wheel motor from Namiko Corp., Tokyo. The rotational speed of the balance wheel motor is preferably a function of the frequency of the pulses that are output. In one preferred embodiment of the invention, the duty cycle of the output pulses is 50%. If this is not possible, the pulse width of the negative or positive component of the pulse should not fall below 5 μs. In one particularly preferred embodiment of the invention, the balance wheel motor has a resolution of 1.8°. In this regard, the driver electronics may drive the motor using microstep technology. The driver electronics may advantageously be set in such a way that 64 pulses further move the motor axle by 1.8°, so that the frequency (F) of the pulse is computed as follows:

$$F[1/s] = \frac{X[°/s]}{1.8°} \cdot 64,$$

where
X [°/S]=the desired angular velocity;
1.8°=the base resolution of the step width of the motor; and
64=the fine resolution of the base resolution of the step width of the motor.

The motor is preferably to be activated to the nominal speed over a period of approximately one second. In one particularly preferred embodiment of the invention, the frequency should not exceed 25 kHz.

Further preferred actuators are galvanic stimulators, the stimulators being designed to act by electrical stimulation of the surface of the body, by electrical stimulation of motor nerves or the musculature, and/or by electrical stimulation of sensory nerves or sensory organs or portions thereof.

In another preferred variant, at least one actuator is a light source, preferably a light source in the field of vision of the wearer of the irradiation apparatus, so that the wearer perceives light stimulation during activity of the actuators. In one preferred variant, the intensity of the light stimulation or the color of the light stimulation is selected in such a way that it has a greater signal effect the greater the amount by which the determined change in the bodily position exceeds the stored standard values.

In another preferred variant, at least one actuator is a sound generator, so that the wearer perceives an acoustic signal during activity of the actuator. In one particularly preferred variant, the sound volume and/or the frequency of the acoustic signal is increase (d) the greater the amount by which the determined change in the bodily position exceeds the stored standard values for the particular spatial quadrant and activities and age groups (see Table 1).

Furthermore, due to the plurality of stored standard values, the device for measuring the change in the bodily position also allows use in the medical and rehabilitation sectors. This is preferably possible due to extensive programmability even in areas involving training of a healthy sense of equilibrium to be further improved, for example in balance exercises in athletics or in the training of military paratroopers. In one preferred variant, a modulator or control knob is used for activating various programs (for example, 1 through 5) that, depending on the design, then activate the actuator from "very mild" (for example, for a gymnast to train balance) all the way to "very severe" (for example, for a patient after a stroke in which portions of the equilibrium center are destroyed). Integration of the device for measuring the change in the bodily position advantageously has a surprisingly wide range in system diversity, since it may be used in the subnormal range for gymnasts, for example, or in the supernormal range for seriously ill patients. Another advantage, previously discussed, is free programmability by selecting individual movement programs, supported by the standard values and the database according to Table 1.

In one preferred variant, the stored standard values for the maximum displacement vectors in the particular spatial quadrants are also individually adapted to the wearer of the irradiation apparatus. For this purpose, it is preferably possible for the wearer of the irradiation apparatus to be able to provide an input concerning which movements he/she perceives as controlled. For example, if a change in the bodily position exceeds a stored standard value for the maximum displacement vector for the particular activity, and an actuator is thereby activated, by making an input the wearer may indicate that the movement was intentional. In this way, the irradiation apparatus learns that the change in the bodily position does not correspond to an uncontrolled movement. In particular, due to the input by the wearer, the exceeded standard value is replaced by a new standard value that corresponds to the change in the bodily position that the wearer has classified as controlled. The standard values for the maximum displacement vectors in the spatial quadrants may thus advantageously be adapted to the equilibrium of the wearer. In particular, optimal use of the irradiation apparatus by wearers with a very highly developed sense of equilibrium, for example gymnasts, is just as possible as use by persons with severe vertigo who experience frequent dizziness, for example. In addition, as a result of this preferred embodiment, the power of the prophylactic photon irradiation may be adapted particularly well to the sense of equilibrium of the wearer. In particular, particularly effective prophylactic photon irradiation for persons who have vertigo is made possible. This was not the case with methods or apparatuses from the known prior art.

In another preferred embodiment, the photon emitter is a laser, particularly preferably a laser diode, very particularly preferably a laser diode comprising a semiconductor material. The preferred selection of a laser or a laser diode as a radiation source for the irradiation apparatus allows particularly precise adjustment of the photon beam power using the output power of the laser. In particular, the output power of lasers or laser diodes is regulatable in a particularly stable manner for long as well as short time periods. The automated control unit may thus control the output power of a laser or a laser diode in a particularly adaptive and precise manner. In addition, lasers or laser diodes in particular emit beams having a low beam divergence. As a result, particularly good focusing of the photon beams, and thus, targeted irradiation of regions or subregions of the inner ear, is possible. Surprisingly, side effects due to the absorption of photons in other tissue regions, for example the outer auditory canal, are thus avoided and wearing comfort is increased. The particularly preferred selection of semiconductor laser diodes is also advantageous for the operation and manufacture of the irradiation apparatus for several reasons. On the one hand, semiconductor laser diodes are inexpensive. On the other hand, due to their small size compared to other types of lasers such as gas lasers, etc., semiconductor laser diodes are particularly suited for being integrated into the irradiation apparatus.

In one very particularly preferred embodiment, the photon emitter is a light emitting diode, very particularly preferably a light emitting diode comprising a semiconductor material. Tests have surprisingly shown that irradiation of the inner ear using light emitting diodes has a particularly great protective effect. In particular, the protective effect of the photon radiation emitted by light emitting diodes is greater than the protective effect of lasers. This may be at least partly attributed to the fact that the light emitting diodes, in contrast to lasers, emit incoherent radiation that preferably activates the protective mechanisms of the sensory hair cells. In addition, it is possible to apply the photon radiation by light emitting diodes in a particularly uniform distribution over the inner ear. As a result, a protective effect is achieved for a particularly large number of sensory hair cells. Furthermore, excellent focusing of the photon beams, and thus, targeted irradiation of regions or subregions of the inner ear, is advantageously possible using light emitting diodes. In particular, side effects that occur due to the irradiation of other tissue regions, for example the outer auditory canal, may be avoided by using light emitting diodes. In addition, it has been shown that the light emitting diodes have very low heat generation, even at high photon beam power. In particular, the outer auditory canal undergoes little or no heating, and wearing comfort is increased. Moreover, light emitting diodes are particularly energy-efficient, since they convert electrical energy to photon radiation with particularly high efficiency. The low heat generation of the light emitting diodes, even at high photon beam power, also facilitates the integration of the light emitting diode into the irradiation apparatus. The overall heat generation of the irradiation apparatus is also reduced when light emitting diodes are utilized as a radiation source. This minimizes potential side effects due to an operation-related increase in the temperature of the irradiation apparatus, and results in a more pleasant feeling for the wearer of the irradiation apparatus. Furthermore, the small size of the light emitting diode is particularly advantageous for integrating it into the irradiation apparatus, and preferably results in a small size and low weight of the overall irradiation apparatus. The small size, low weight, and low heat generation of the preferred irradiation apparatus made possible by using light emitting diodes is particularly advantageous for wearing acceptance, and allows protective use of the irradiation apparatus over a long period of time.

In one very particularly preferred embodiment, the wavelength of the photon beams is between 600 nm and 1200 nm, preferably between 700 nm and 900 nm, particularly preferably at 790 nm and 820 nm, and in particular is 808 nm. In particular, it has surprisingly been shown that the protective effect of photon radiation on the inner ear is a function of the wavelength of the photon beam. In particular, it has been shown that the irradiation of the inner ear with light having a wavelength in the near infrared range between 600 nm and 1200 nm, preferably between 700 nm and 900 nm, and particularly preferably at 790 nm and 820 nm, in particular 808 nm, has a particularly great protective effect on the inner ear, and thus effectively prevents the development or exacerbation of hearing impairment and/or vertigo. 808 nm is in particular also intended to mean 807.5 nm, 808.8 nm, 806.9 nm, or 808.2 nm by way of example. Similarly, 790 nm is in particular also intended to mean 789.2 nm, 791.2 nm, 788.7 nm, or 790.3 nm by way of example. Likewise, 820 nm is in particular also intended to mean 821.4 nm, 818.3 nm, 819.1 nm, or 820.5 nm by way of example.

The particularly strong prophylactic effect of the photon beams according to the particularly preferred ranges may be attributed in particular to the absorption spectrum of molecules that are involved in the mechanism for protecting the sensory hair cells. As described above, in particular cytochrome c oxidase (CCO) plays a key role in the mechanism on which the protective effect of the irradiation apparatus according to the invention is based. In particular, due to an overlap of the mentioned preferred wavelength ranges with the absorption spectrum of CCO, the photon irradiation according to the invention thus has a particularly great protective effect on the sensory hair cells. In addition, the dispersion or the scattering of the photon radiation in biological tissue is a function of the wavelength. Tests have shown that photon radiation having a wavelength between 600 nm and 1200 nm, preferably between 700 nm and 900 nm, and particularly preferably at 808 nm, has a particularly suitable scattering behavior in the tissue of the inner ear. Due to this suitable scattering behavior, in particular the photon radiation also reaches sensory hair cells in deeper tissue layers. As a result, a particularly great protective effect may be achieved, and hearing impairment and/or vertigo may be prevented in a particularly effective manner when the inner ear is irradiated, using the irradiation apparatus according to the invention, with photons having the mentioned preferred wavelength.

In particularly preferred embodiments, the laser diodes or the light emitting diodes comprise a semi-finished material selected from the group comprising gallium arsenide (GaAs), aluminum gallium arsenide (AlGaAs), indium gallium arsenide (InGaAs), gallium arsenide phosphide (GaAsP), aluminum gallium indium phosphide (AlGaInP), and gallium phosphide (GaP), gallium arsenide phosphide (GaAsP), aluminum gallium indium phosphide (AlGaInP), and gallium phosphide (GaP). These semiconductor materials are particularly suited for generating photon beams in the near infrared range. In particular, the materials are particularly suited for generating, with high efficiency, photon beams having wavelengths of 600 nm and 1200 nm. In addition, laser diodes or light emitting diodes manufactured using these semiconductor materials are particularly cost-effective and energy-efficient, and generate photon beams with low heat generation.

In another preferred embodiment, the automated, measuring data-based control unit may set the output power of the photon emitter in a range between 0.1 mW and 1000 mW, preferably between 0.5 mW and 300 mW, particularly preferably between 1 mW and 120 mW. Irradiation of the inner ear with a photon beam power of the mentioned increasingly smaller ranges is particularly suited for preventing damage to the sensory hair cells. The electronic design of the automated, measuring data-based control unit therefore preferably allows particularly precise regulation of the output power of the photon beam in the mentioned ranges. Particularly adaptive control of the photon power in the biologically relevant power range is thus possible due to a preferred precise, rapid control of the output power between 0.1 mW and 1000 mW, preferably between 0.5 mW and 300 mW, particularly preferably between 1 mW and 120 mW. This results in an increased prophylactic effect of the irradiation apparatus on the inner ear. In particular, the irradiation of the inner ear with photon beam power in the particularly preferred range of 1 mW to 120 mW in combination with the particularly preferred wavelength ranges of the photon radiation at 790 nm, 820 nm, or in particular 808 nm, results in a particularly protective effect on the auditory and vestibular structures of the inner ear. The particularly effective prophylaxis of hearing impairment and/or vertigo thus achieved is not known from the prior art.

In one particularly preferred embodiment, the photon beam is conducted by a photon beam conduction system. The experimental comparison of various embodiments has shown that it is particularly advantageous for the photon emitter not to irradiate protons directly onto the inner ear, but, rather, for the protons to be conducted by a photon beam conduction system onto the entire inner ear or predetermined regions of the inner ear. It has been possible to achieve a particularly great prophylactic effect when the preferably irradiated, predetermined regions of the inner ear preferably involve the cochlea and the vestibule, comprising the otolith organs and ampullae of the auditory canals. This has preferably been achieved by conducting the photon beam through the photon beam conduction system in such a way that the photon beam has a preferred diameter of 12-18 mm, particularly preferably 15 mm, during irradiation of a region of the inner ear. The mentioned preferred dimension is not easily derivable from the anatomy of the inner ear. In particular, a smaller diameter would be selected based on the anatomy.

That is, the dimensions and properties of the apparatus do not involve a selection from common sizes and properties, that for those skilled in the art are only one design possibility that they would provide without inventive activity.

However, the preferred diameters advantageously and surprisingly result in a particularly great protective effect. This is due, at least in part, to an unexpected focusing effect of the photon beams as they pass through tissue layers situated in front of the sensory hair cells.

In particularly preferred embodiments, the photon beam conduction system also comprises a system comprising lenses and/or mirrors that bundle, expand, or collimate the photon beam. This system made up of lenses and mirrors makes it possible in particular to adjust the photon beam in such a way that it irradiates a predetermined region of the inner ear, and when incident on the inner ear has a preferred diameter of 12-18 mm, particularly preferably 15 mm. These diameters do not involve a selection from common sizes and properties that for those skilled in the art are only one design possibility that they would provide without inventive activity. As a result of the homogeneous irradiation of the cochlea and the vestibule of the inner ear, which is thus preferably achieved, the photon beam develops a protective effect on a surprisingly large number of sensory hair cells.

In another preferred embodiment, the photon beam conduction system comprises an optical fiber cable that has a preferred outer diameter of 1 to 8 mm, particularly preferably 3 mm to 5 mm. The optical fiber cable preferably has a flexible design. The optical fiber cable is thus able to conduct the photon beam from the radiation source to the inner ear. That is, the dimensions and properties of the apparatus do not involve a selection from common sizes and properties, which for those skilled in the art are only one design possibility that they would provide without inventive activity. In particular, as a result of the preferred outer dimensions of the optical fiber cable, in one preferred embodiment the irradiation apparatus may be inserted into the outer auditory canal and may have a particularly good hold at that location. The insertion of an optical fiber cable thus results in a particularly high level of wearing comfort for the wearer of the irradiation apparatus, which increases the compliance of the wearer and thus the effective irradiation period. In particularly preferred embodiments, the optical cable comprises glass fibers or polymeric optical fibers. These materials have particularly high effectiveness in relaying the photon radiation, and thus preferably result in energy-efficient irradiation of the inner ear. In addition, the reduction of losses of photon power in the optical fiber cable due to the use of glass fibers or polymeric optical fibers results in decreased heat generation, which surprisingly increases comfort for the wearer of the irradiation apparatus. Since even only a small amount of heat generation results in an uncomfortable feeling for the wearer, the preferred embodiment greatly increases wearing acceptance.

In one preferred embodiment, the photon emitter and/or the photon beam conduction system are/is present embedded in a retaining device that comprises a rod-shaped shaft having an opening and/or a window positioned at one end such that at least part of the photon beam exits the opening or the window. In one particularly preferred embodiment, the rod-shaped shaft also has a diameter of 0.5 mm to 1 mm and a length of 3 mm to 5 mm. As the result of such a preferred configuration of a retaining device, the irradiation apparatus is particularly easily insertable into the outer auditory canal, and effectively irradiates the inner ear. The mentioned preferred lengths and dimensions do not automatically result from the anatomy of the outer auditory canal of the wearer. Instead, they are selected to be smaller, so that it was very surprising that the preferred lengths and diameters allow particularly secure positioning of the apparatus in the ear, also for athletics (even for horseback riding or diving). Due to the geometric configuration of the retaining device, use of the irradiation apparatus for effective prophylactic irradiation of the inner ear may be carried out particularly easily and reliably. In particular, the geometric configuration of the retaining device, and in particular the dimensions of the rod-shaped shaft, ensure effective irradiation of the preferred regions of the inner ear, comprising the cochlea and vestibule. In particular, the situation is thus avoided that the inner ear is not sufficiently homogeneously irradiated. Furthermore, in particular the situation is avoided that regions that are not part of the inner ear are irradiated, thus resulting in undesirable side effects.

In one very preferred embodiment, at one end the rod-shaped shaft has a silicone shield with a diameter of 3 mm to 15 mm. During use of the irradiation apparatus in which the apparatus is inserted into the outer auditory canal, the silicone shield results in surprisingly stable positioning of the apparatus in the outer auditory canal, and thus results in surprisingly accurate irradiation of the preferred region of the inner ear, comprising the cochlea and vestibule. In addition, the silicone shield has particularly high biocompatibility and increases wearing comfort. Wearing the irradiation apparatus over an extended period of time, and accompanying long-term preventive irradiation, are thus facilitated to a great extent by the silicone shield. Furthermore, the silicone shield surprisingly prevents bacteria and pathogens from penetrating through the outer auditory canal, thus additionally protecting the inner ear. In addition, the silicone shield results in particularly damping support of the photon emitter, which surprisingly results in particularly homogeneous photon irradiation of the inner ear, even during dynamic activities such as athletics, dancing, or climbing stairs.

In one preferred embodiment, the irradiation apparatus is present in combination with a hearing aid. The prophylactic photon irradiation is advantageously particularly meaningful for persons who already have hearing damage, in particular for patients with hearing impairment. As described, a particularly great protective effect may be achieved in particular by adapting the irradiation power to the state of the inner ear, in particular to the hearing of the wearer of the irradiation apparatus. In particular, further deterioration of hearing may be effectively prevented by using the preventive irradiation apparatus. The combination of the irradiation apparatus with a hearing aid advantageously increases wearing acceptance for the irradiation apparatus. The prophylactic irradiation therefore takes place over the entire time that the hearing aid is worn, in particular all day for 10 hours or more daily. A patient with hearing impairment is accustomed to such wearing, in particular due to wearing a hearing aid for many years, and does not perceive the additional integration of a photon emitter as burdensome. In contrast, test subjects wear an irradiation apparatus combined with a hearing aid even more frequently than just a hearing aid, since they are additionally motivated by the simultaneous prophylactic irradiation. The combination of the irradiation apparatus with a hearing aid advantageously also increases wearing comfort. Due to a preferred integration of the photon emitter into a hearing aid, it is advantageously necessary to introduce only the hearing aid into the outer auditory canal. The inner ear may surprisingly be irradiated in a particularly stable and reliable manner by such an integration of the photon emitter into a hearing aid. In one preferred embodiment, the irradiation apparatus is combined with a sound-amplifying hearing aid, preferably combined with a behind-the-ear device or an in-the-ear device. One preferred combination of the irradiation apparatus with a behind-the-ear device is illustrated in FIG. 3. One preferred combination of the irradiation apparatus with an in-the-ear device is illustrated in FIG. 4. Surprisingly, irradiation of the inner ear by the combination of the irradiation apparatus with a behind-the-ear device or an in-the-ear device is particularly advantageous. Surprisingly homogeneous irradiation of the inner ear is made possible due to an arrangement of the photon emitter with preferably multiple light emitting diodes in a ring at the end of the hearing aid. In particular, a protective effect of the photon irradiation on a particularly large number of sensory hair cells is thus made possible. In addition, it was very surprising that the integration of photon emitters into the sound-amplifying hearing aids does not compromise the function of the sound-amplifying hearing aids. Furthermore, it was very surprising that functional synergies result from the combination of the irradiation apparatus with a sound-amplifying hearing aid. The microphone of the hearing aid may thus likewise advantageously be used for measuring otoacoustic emissions. Moreover, the measuring microphone of the sound-amplifying device may be used for determining the ambient noise level, in particular the sound pressure level in the surroundings. In addition, the sound generator of the hearing aid may advantageously be used for emitting acoustic signals for exciting otoacoustic emissions. The sound generator of the sound-amplifying hearing aid may preferably also be utilized as an actuator in order to transmit to the wearer an acoustic warning signal of the irradiation apparatus that indicates that the change in the bodily position exceeds a standard value. It was very surprising that such a two-fold and even three-fold functional utilization of a sound generator or a measuring microphone is possible for measuring acoustic signals, for measuring evoked otoacoustic emissions, for training the sense of equilibrium via warning signals, and for a sound-amplifying hearing aid. The combination of an irradiation apparatus with a sound-amplifying hearing aid has thus resulted in a surprisingly cost-effective and energy-efficient embodiment.

In another preferred embodiment, the hearing aid is an implantable hearing aid or a cochlea implant. The combination of the irradiation apparatus with an implantable hearing aid or a cochlea implant is particularly advantageous, since this allows long-term preventive irradiation of the inner ear daily for up to 24 hours a day over multiple months or years. In addition, the combination of the irradiation apparatus with an implantable hearing aid or a cochlea implant results in particularly stable embedding of the irradiation apparatus, and thus results in particularly stable irradiation of the inner ear. Furthermore, by combining the irradiation apparatus with an implantable hearing aid or a cochlea implant, the photon emitter or the photon beam conduction system may preferably be positioned particularly close to the auditory and/or vestibular structures of the inner ear. This results in a particularly increased protective effect due to use of the irradiation apparatus according to the invention, and prevents damage to hearing and/or equilibrium over the long term in a surprisingly effective manner.

In one preferred embodiment, components of the irradiation apparatus according to the invention are connected to one another for wireless data transmission, preferably using Bluetooth technology. Thus, for example, preferably at least two components, selected from a group comprising the automated, measuring data-based control unit for controlling the output power of the photon emitter, the device for measuring acoustic signals of the surroundings, the device for measuring evoked otoacoustic emissions of the inner ear, and the device for measuring the change in the bodily position of the wearer, are connected to one another for wireless data transmission, preferably using Bluetooth technology.

The invention further relates to a system for the protective irradiation of the inner ear of a wearer for the prophylaxis of hearing impairment and/or vertigo, comprising an irradiation apparatus according to the invention, wherein
 a) signals concerning the wearer of the irradiation apparatus and/or the surroundings of the wearer are measured,
 b) the output power (P) of the photon emitter for the protective irradiation of the inner ear is computed based on these measuring data,
 c) the output power of the photon emitter is set to the computed value P, and the irradiation of the inner ear takes place with the photon beam power P.

In the system according to the invention, which involves a group of interconnected or operatively connected apparatus elements, multiple apparatus components interact with one another to achieve the aim of the invention. The object according to the invention may surprisingly be achieved particularly well with this system.

In addition to the apparatus, the use of the apparatus, and the system, which comprises the apparatus according to the invention together with other components, the invention also further relates to a method for the protective irradiation of the inner ear for the prophylaxis of hearing impairment and/or vertigo, using the irradiation apparatus according to the invention, the method comprising:

a) measuring signals concerning the wearer of the irradiation apparatus and/or the surroundings of the wearer,
 b) computing, based on these measuring data, the output power (P) of the photon radiation for the protective irradiation of the inner ear,
 c) controlling the output power of the photon emitter to the computed value P and irradiating the inner ear with the photon beam power P.

Technical features that have been disclosed for the method according to the invention for the protective irradiation of the inner ear for the prophylaxis of hearing impairment and/or vertigo also apply in particular to the irradiation apparatus according to the invention and to the system according to the invention. The average person skilled in the art is aware that in particular the features of the preferred embodiments of the method according to the invention may also be used for the technical description of the irradiation apparatus according to the invention and the system according to the invention (for example, in conjunction with the [method] according to the invention, a preferred sound pressure level limiting value of 85 dB is disclosed; it is apparent to those skilled in the art that this preferred sound pressure level limiting value may advantageously also be used for the irradiation apparatus according to the invention and/or for the system according to the invention).

That is, features of the method for the protective irradiation of the inner ear for the prophylaxis of hearing impairment and/or vertigo as well as features of the preferred embodiments of this method may likewise be used by the average person skilled in the art for the irradiation apparatus according to the invention, for the use thereof, and for the system for the protective irradiation of the inner ear. Embodiments of the irradiation apparatus according to the invention in particular preferably have features that are suitable for carrying out the method and preferred embodiments of the method. Disclosed technical features that have been disclosed in conjunction with the method and the preferred embodiments may thus be achieved in particular also with the irradiation apparatus according to the invention and the apparatus system, the system according to the invention, for the protective irradiation of the inner ear.

Hearing impairment and/or vertigo may surprisingly be prevented in a particularly effective manner using the method for irradiating the inner ear. By measuring signals concerning the wearer of the irradiation apparatus, in particular data may be recorded that provide information about the functionality of the sense of hearing or equilibrium of the wearer of the irradiation apparatus. These data preferably describe the state of the auditory and/or vestibular structures of the inner ear of the wearer of the irradiation apparatus. The auditory and/or vestibular structures comprise in particular the outer sensory hair cells, the spiral ganglion cells, the inner sensory hair cells, and downstream neurons for processing acoustic signals and signals for determining the bodily position. Such data are preferably obtained by measuring evoked otoacoustic emissions. Furthermore, as the result of measuring signals concerning the surroundings of the wearer, data concerning external factors are incorporated into the method that influence the state of the auditory and/or vestibular structures of the wearer. These environmentally-related factors (external factors) include in particular the ambient noise level. An increased sound level due to noise results in particular in impairment of the state of the inner ear, i.e., an impairment of the functionality of the inner ear for the sense of hearing and/or equilibrium. The impairment of the state of the inner ear may be attributed in particular to a degenerative development of the auditory and/or vestibular structures of the inner ear. The method, using the irradiation apparatus, preferably counteracts such degenerative development. Degenerative development of the inner ear is counteracted in a particularly effective manner due to computing the output power (P) of the photon radiation for the protective irradiation of the inner ear, based on the measuring data concerning the wearer of the irradiation apparatus and/or the surroundings of the wearer, and controlling the output power to this computed value. Adapting the output power to needs of the wearer of the irradiation apparatus surprisingly shows a particularly great prophylactic effect compared to prophylactic methods that irradiate the inner ear at a constant power. Method steps a) through c) may preferably be carried out multiple times in succession at regular intervals. The irradiation period of the method may preferably be more than 10 hours a day, and may take place over multiple days, weeks, months, or years. Due to continuously recording measuring data and adapting the photon beam power to these measuring data, prophylactic irradiation with optimal adaptation to the protective functional mechanism of photon irradiation of the inner ear is possible. As described above, experiments have shown that the protective effect of photon irradiation of the inner ear depends critically on the power of the photon irradiation. In particular, the functional mechanism of the protective photon stimulation comprises excitation of transmembrane complexes of the respiratory chain, in particular comprising cytochrome c oxidase. In addition, the protective functional mechanism of the photon irradiation in particular has a two-phase dependency on the photon beam power. As shown by experiments, the result in particular is that photon beam power that is too low achieves only a slight protective effect. Furthermore, the protective effect is not continuously increased by continuously increasing the photon beam power. Instead, as the result of the photon beam power being too high, the auditory and/or vestibular structures are adversely affected by the excessively high photon radiation and may degenerate. Photon radiation that is too high therefore results in only a slight protective effect, or even results in side effects. Surprisingly, excessively high photon beam power therefore does not result in effective prophylaxis of hearing impairment and/or vertigo, and instead may even result in a minimized protective effect due to the occurrence of undesirable side effects. Setting the photon beam power to an optimal value that is computed based on measuring data surprisingly shows a particularly great protective effect. Setting the photon radiation in the method to a value that is optimized for prophylaxis of hearing impairment or vertigo may be advantageously implemented by the automated, measuring data-based control unit.

In one preferred variant, the measuring data comprise evoked otoacoustic emissions of the outer hair cells of the inner ear, and at least one first parameter A for computing the output power P of the photon radiation is determined based on these measuring data. The measurement of evoked otoacoustic emissions advantageously reflects the state of the sensory hair cells of the inner ear. Sensory hair cells have a high level of functionality for the perception of acoustic signals and/or equilibrium when they are stimulated to emit otoacoustic emissions. It is thus advantageously possible to set the output power of the photon radiation to a value that is optimal for the prophylactic irradiation, and that is computed by taking into account the state of the sensory hair cells of the inner ear, i.e., the effective functionality of the inner ear as the organ for the sense of hearing and/or equilibrium. Based on standard literature such as the above-mentioned *Otoacoustic Emissions—Clinical Applications*, among others, those skilled in the art are familiar with suitable methods for measuring otoacoustic emissions and computing biologically relevant parameters. In one particularly preferred variant, the parameter of reproducibility is determined in the method, using otoacoustic emissions. Multiple acoustic signals are hereby transmitted to the inner ear, and for each of these acoustic signals it is determined whether an otoacoustic emission has been evoked by the acoustic signal. Reproducibility is computed from the ratio of the number of detected, evoked otoacoustic emissions to the number of emitted acoustic signals. For example, if a total of 100 acoustic signals are emitted, and of these 100 signals, 60 otoacoustic emissions are detected, the reproducibility is 60%. Reproducibility, as a particularly informative parameter, advantageously reflects the functionality of the inner ear for responding to acoustic signals. Reproducibility is therefore a particularly relevant parameter for determining the biological function of the inner ear. In one particularly preferred variant, reproducibility is determined once per month, using the otoacoustic emissions.

In another preferred variant, the measuring data comprise acoustic signals from the surroundings of the wearer, and at least one second parameter B for computing the output power P of the photon radiation is determined from these measuring data. By measuring acoustic signals from the surroundings of the wearer, it is advantageously possible to record measuring data that provide information concerning the stress on the inner ear due to acoustic irradiation. The auditory and vestibular structures of the inner ear may be damaged from a high level of acoustic irradiation in particular due to ambient noise, for example construction noise, engine noise, or loud music. An optimal value for the irradiation power may advantageously be set in the method by adapting the photon beam power to the ambient noise. A particularly great protective effect on the inner ear, comprising in particular noise-sensitive sensory hair cells, may be achieved in this way. Those skilled in the art are familiar with methods by which informative parameters concerning the ambient noise may be determined. In one preferred variant, the parameter B, which [represents] the ambient noise level, quantifies the sound pressure level. In one particularly preferred variant, the sound pressure level is determined in a preferred sound frequency range of 250 Hz to 8000 Hz, particularly preferably in dB (A) weighting. The sound pressure level, in particular in the mentioned frequency ranges, is a particularly good measure for the biological stress experienced by the inner ear due to ambient noise.

In another preferred variant, the measuring data comprise changes in the bodily position of the wearer of the irradiation apparatus, and at least a third parameter C for computing the output power P of the photon radiation is determined from these measuring data. By adapting the photon beam power to measuring data concerning the change in the bodily position, the protective photon irradiation may be adapted to the state of the sense of equilibrium or to factors that influence the state of the sense of equilibrium. In particular, an advantageous protective effect has been determined when the photon irradiation is increased when there is a disturbance in the sense of equilibrium. A disturbance in the sense of equilibrium manifests in persons in particular by an increased change in the bodily position as occurs during swaying or falling, for example. The parameter C preferably describes the extent by which the change in the bodily position exceeds standard values for intentional movements. In one particularly preferred embodiment, the change in the bodily position is determined as a function of the spatial displacement vectors, using gyrometers. The parameter C particularly preferably determines the percentage by which the change in the bodily position exceeds stored standard values for maximum displacement vectors in the spatial quadrant for the particular activity and the particular age group.

In one preferred variant, the output power of the photon beam is computed from the sum of three positive summands, wherein the first summand PA is computed using parameter A, the second summand PB is computed using parameter B, and the third summand PC is computed using parameter C, and if the sum of PA, PB, and PC exceeds a maximum value M, then P=M. The overall irradiation is thus advantageously computed on a proportional basis from summands that are based either on parameters that provide information concerning the state of the inner ear, or factors that influence the state of the inner ear. In particular, parameter A (computed from measuring data concerning the otoacoustic emissions) relates to the functionality of the inner ear for the sense of hearing, and parameter C (computed from measuring data concerning the change in the bodily position) relates to the functionality of the inner ear for the sense of equilibrium. Furthermore, parameter B (computed from measuring data concerning ambient acoustic signals) relates in particular to the stress on the inner ear due to ambient noise, and thus in particular, relates to potential damage to the inner ear and impairment of its functionality as the organ of the senses of hearing and equilibrium. In one preferred variant, the photon beam power does not exceed a maximum value. For this purpose, the measuring data-based control unit controls the power of the photon emitter, preferably in such a way that the power of the photon emitter does not exceed a maximum value of preferably 120 mW to 300 mW. Upon reaching a maximum value for the power with which the inner ear is irradiated, preferably upon reaching a maximum value for the power with which the inner ear is irradiated that is between 120 mW and 300 mW, side effects may occur due to heating and/or overdosing of the photon beam power. Side effects of the protective irradiation may be minimized and/or avoided in the method by regulating the computer-controlled control unit so that a maximum value of the photon radiation is not exceeded. As the result of the power of the photon irradiation not exceeding 300 mW, in particular 120 mW, unintentional heating of the inner ear, overstimulation of the sensory hair cells, and other side effects that include dizziness and/or hearing impairment may be minimized and/or avoided.

In one particularly preferred variant, parameter A, which is determined by measuring the evoked otoacoustic emissions, is reproducibility, and the summand of the photon beam power PA, which is based on parameter A, is a monotonically decreasing function of A. The intensity of the photon irradiation of the inner ear is thus advantageously increased when the reproducibility of the measurement of otoacoustic emissions decreases. As described above, reproducibility reflects in particular the capability of sensory hair cells to perceive acoustic signals. It has advantageously been shown that a particularly great prophylactic effect may be achieved when the photon irradiation is increased the poorer the state of the inner ear, i.e., the lower the reproducibility. In one particularly preferred variant, for A≥59%, PA=1 mW and for A<59%, PA=(60%−A)*1 mW. As the result of such a computation, PA, as the base value for the irradiation, is set at 1 mW for a reproducibility of greater than or equal to 59%. A reproducibility value that is greater than or equal to 59% indicates a good sense of hearing and a high level of functionality of the sensory hair cells. For such reproducibility, the base value for the photon irradiation is thus advantageously set to 1 mW based on the otoacoustic emissions. However, if reproducibility of less than 59% is present, this is an indication that the functionality of the sensory hair cells is impaired. This may be due to the fact that the wearer has too few sensory hair cells, for example because sensory hair cells have died, or because a majority of the remaining sensory hair cells have only a reduced response to acoustic stimulation. In this case, a method for prophylactic irradiation in which the proportional photon beam power PA increases linearly when reproducibility decreases has proven to be particularly effective. It has surprisingly been shown that in particular a linear increase of PA as a function of decreasing reproducibility A (PA=(60%−A)*1 mW for A<59%) results in an optimal power level for the photon irradiation that counteracts degenerative development of the auditory or vestibular structures of the inner ear particularly well.

In one particularly preferred variant, the second parameter B, which is determined by measuring acoustic signals from the surroundings of the wearer, is the sound pressure level, and the summand of the photon beam power PB, which is based on parameter B, is a monotonically increasing function of B. As described in the preceding paragraphs, the sound pressure level of the ambient noise level is a particularly suitable parameter for quantifying the potential stress on the inner ear due to acoustic signals from the surroundings. This is the case in particular in one particularly preferred variant in which the sound pressure level is determined in a frequency range of 250 Hz to 8000 Hz in dB (A) weighting. When an increased sound pressure level is measured in the surroundings by the irradiation apparatus, the inner ear is subjected to stress by the increased ambient noise level, and the auditory or vestibular structures of the inner ear may be damaged. It has surprisingly been shown that an increase in the irradiation power on the inner ear during an increased sound pressure level in the surroundings prevents damage to hearing and/or equilibrium in a particularly effective manner. In particular, it has been shown that for sensory hair cells that have been subjected to stress by an increased sound pressure level, for example due to noise, damage may be avoided when the sensory hair cells are irradiated with photons beforehand or at the same time. This may be attributed, at least in part, to the fact that the protective effect of the photon irradiation, due, among other things, to the excitation of cytochrome c oxidase as described above, is optimized when the sensory hair cells subjected to stress by noise are irradiated with increased output power of the photon emitter. Damage to the auditory or vestibular structures of the inner ear due to an increased ambient noise level may advantageously be avoided particularly well when the inner ear is irradiated with photons prior to or at the same time as the noise exposure. In addition, prophylactic irradiation that is adapted to the ambient noise level results in a particularly great protective effect. This means that, in particular when the inner ear of the wearer is prophylactically irradiated over an extended period of preferably at least one week for preferably at least 3 hours daily, even a subsequent high noise exposure level of above 100 dB, for example, results in very minor hearing damage. Prophylactic photon irradiation that is adapted to the everyday noise exposure level thus also prevents in particular hearing impairment that would occur due to a very high subsequent noise exposure level. The protective mechanism of the photon irradiation thus prevents not only hearing impairment that occurs due to a stress during the irradiation, but also in particular hearing impairment that may occur due to subsequent stresses, for example due to noise.

In one preferred variant, the proportional photon beam power PB is 0 mW for values of the sound pressure level B, measured in the surroundings, which are below a sound pressure level limiting value G. In one preferred variant, the value of the sound pressure level limiting value is between 75 dB and 95 dB, preferably approximately 85 dB, whereby "approximately 85 dB" means 85.3 dB, 85.9 dB, 83.5 dB, 84.7 dB, 86 dB, or 85.0 dB, for example. Tests have surprisingly shown that the protective effect of the photon irradiation is particularly great when the inner ear is subjected to stress by acoustic irradiation that is characterized by a sound pressure level that is higher than the sound pressure level limiting value, in particular for the mentioned regions that become increasingly smaller. For a sound exposure to the inner ear that is below a limiting value for the sound pressure level, increasing the photon irradiation as a function of the sound pressure level does not result in a particularly increased protective effect. Below the sound pressure level limiting value, irradiation therefore preferably takes place at a power P=PA+PC. With regard to the ambient noise level, the power component summands PA and PC may therefore be understood as base values. The inner ear is irradiated at the base power P=PA+PC when the wearer of the irradiation apparatus is in an environment in which the ambient noise level does not subject the inner ear to particularly high stress, i.e., in particular when the sound pressure level is below the sound pressure level limiting value.

The stress on the inner ear due to an ambient noise level is increased in particular at or above a limiting sound pressure level of 70 dB, in particular at or above 85 dB, and results in damage to the inner ear that is more severe the higher the sound pressure level. Damage to the inner ear may be avoided in a particularly effective manner by increasing the power of the protective photon irradiation as a function of the sound pressure level at or above the limiting value G.

In one very preferred embodiment, when a sound pressure level limiting value is reached, the proportional power of the photon beam PB is set to $PB=2^{floor((B-G)/3\ dB)+1}*(PA+PC)-(PA+PC)$. "Floor" refers to the rounding function that rounds a real number to the next smaller integer. That is, in particular the floor of a real number R is equal to the integer N for which N≤R and N+1>R is valid; for example, floor(3, 3)=3. As described in the preceding paragraphs, PA and PC are summands of the photon power that are independent of the value of the measured sound pressure level. In particular, the sum of PA and PC is the value of the photon beam power with which the inner ear is irradiated when the ambient noise level is below the sound pressure level limiting value G. PA+PC is thus also referred to as the base power. By determining PB from $PB=2^{floor((B-G)/3\ dB)+1}*(PA+PC)-(PA+PC)$ for values of the sound pressure level B that are greater than or equal to the sound pressure level limiting value G, the resulting total power P for B≥G is thus $P=2^{floor((B-G)/3\ dB)+1}*(PA+PC)$. When the sound pressure level limiting value is reached, i.e., for B=G, P=2*(PA+PC), and thus corresponds to twice the value of the base power (PA+PC). The power of the photon irradiation is doubled with each further increase of the sound pressure level B by 3 dB. As a result of the rounding function in the exponent of $P=2^{floor((B-G)/3\ dB)+1}*(PA+PC)$, the photon beam power is increased when a value of B in each case exceeds G by a difference of 3 dB or integral multiples thereof. High volatility of the photon beam power due to measurement fluctuations during the determination of the sound pressure level is advantageously avoided in this way. The described doubling of the photon beam power when the sound pressure level rises by 3 dB surprisingly has a particularly great protective effect. It has been shown in experiments that such an increase in the power of the photon beam results in a particularly great protective effect on the inner ear, so that no damage, or greatly reduced damage, to the inner ear, in particular to the sensory hair cells, spiral ganglion cells, and neurons, results from an increased ambient noise level. The photon beam power of $2^{floor((B-G)/3\ dB)+1}*(PA+PC)$ that is set for B≥G is optimally adapted to the stress on the inner ear due to an increased ambient noise level. In particular, the described adaptation of the photon beam power allows individualized prophylactic irradiation of the inner ear that is optimally adjusted to the potential for damage from the ambient noise. The wearing acceptance of the device is thus increased, and long-term prophylactic irradiation over the entire day is made possible. This surprisingly results in much more effective prevention of hearing and equilibrium impairment compared to preventive irradiation with irradiation power provided independently of the ambient noise.

In another very particularly preferred variant, the parameter C is preferably determined once weekly, once monthly, or once semi-annually by conducting a standardized balance test, and is computed from the forward, backward, and/or lateral movements of the wearer of the irradiation apparatus, based on standard values that are specific to age, gender, and exercise. C is very particularly preferably measured in %, and corresponds to the standard balance deficit test (SBDT) composite score. The SBDT is a standardized balance test in which the wearer of the irradiation apparatus performs various exercises. In particular, the balance test preferably comprises the following exercises:

Standing on two legs with eyes open
Standing on two legs with eyes closed
Standing on one leg with eyes open
Standing on one leg with eyes closed
Eight tandem steps (one foot in front of the other) with eyes open
Standing on two legs with eyes open on a foam support surface (height 10 cm, density 25 kg/m³) and standing on two legs with eyes closed on a foam support surface
Standing on one leg on a foam support surface
Eight tandem steps on a foam support surface
Walking 3 m while rotating the head
Walking 3 m while alternately turning the head to the left and right in rhythm
Walking 3 m nodding the head in rhythm
Walking 3 m with eyes closed
Walking over four barriers, with a barrier height of 26 cm and a distance of 1 m between the barriers
Sitting down and standing up For each of these exercises, a determination is made, using the device for measuring the change in a bodily position, concerning the extent by which the change in the bodily position deviates from standard values for the particular age group. The SBDT composite score quantifies the deviation of the change in the bodily position from the standard values, and is computed as follows:

$$SBDT\ \text{composite score} = \frac{\left(\sum_i pi + \sum_i ri\right)*100}{n*400}$$

In this regard, n refers to the number of exercises performed during the balance test. The index i refers in each case to the ith exercise, and is thus i=1, 2, . . . , n.

In addition, pi is equal to the "pitch sway" measured during the ith exercise, divided by the standard value of the pitch sway for the ith exercise for the corresponding age group in %, whereby the pitch sway quantifies the forward and backward swaying movements of the wearer. The pitch sway is preferably determined, using the device for measuring the change in the bodily position, comprising a gyrometer, as the angular velocity in °/s along the y reference axis, and preferably corresponds to the median y value of the displacement vectors that are determined during the ith exercise. Furthermore, ri is equal to the "roll sway" measured during the ith exercise, divided by the standard value of the roll sway for the ith exercise for the corresponding age group in %, whereby the roll sway quantifies the lateral swaying movements of the wearer. The roll sway is preferably determined, using the device for measuring the change in the bodily position, comprising a gyrometer, as the angular velocity in °/s along the x reference axis, and preferably corresponds to the median x value of the displacement vectors that are determined during the ith exercise.

If, for example, the body sway of the wearer of the apparatus corresponds to the standard values for the particular exercise, i.e., pi and ri are equal to 100% for all ith exercises, the SBDT composite score is equal to 50%. An SBDT composite score of less than 50% indicates that the body sway of the tested person during the exercises is less than the standard values for the corresponding age group. A low SBDT score, in particular an SBDT score of less than 50%, thus indicates a good sense of equilibrium. In addition, an SBDT composite score of greater than 50% indicates that the body sway of the tested person during the exercises is greater than the standard values for the corresponding age group. A high SBDT score, in particular an SBDT score of greater than 50%, thus indicates a diminished sense of equilibrium.

In one particularly preferred variant, C corresponds to the SBDT composite score, and for C less than 50%, PC=0 mW, and for C greater than or equal to 50%, PC=(C−45%)*0.2 mW. In this preferred embodiment, the photon beam power, based on the measuring data concerning the change in the bodily position, is advantageously not increased when the tested wearer of the irradiation apparatus has an SBDT composite score of 50% or less. In this case, the wearer has a good sense of equilibrium, and an optimal protective effect is preferably achieved with a photon beam power of P=PA+ PC. For an SBDT composite score of greater than or equal to 50%, PC=(C−45%)*0.2 mW, and the photon power is thus increased linearly with the SBDT composite score. For an SBDT composite score of 55%, for example, and thus C=55%, PC=2 mW, and for C=60%, PC=3 mW, and so forth. Linearly increasing the photon beam power for persons with an increased SBDT composite score, and thus a diminished sense of equilibrium, advantageously results in a particularly great protective effect. Hearing impairment and/ or vertigo are/is surprisingly prevented to a particularly great extent by such an adaptation of the photon beam power to the sense of equilibrium of the wearers of the apparatus. In particular, further exacerbation of the vertigo may be prevented in a particularly effective manner by increasing the power of the photon radiation as a function of the severity of the vertigo. Vertigo is frequently attributable to reduced functionality or number of sensory hair cells in the inner ear, in particular in the vestibule. The preferred increase in the photon radiation in the case of vertigo is therefore adapted to the state and/or the number of sensory hair cells, and thus increases in particular the protective effect on the sensory hair cells.

BRIEF DESCRIPTION OF THE DRAWINGS

Further objectives, features, advantages, and applications of the apparatus according to the invention result from the following description of exemplary embodiments with reference to the drawings. All features that are described and/or graphically illustrated, alone or in any arbitrary combination, constitute the subject matter of the invention, regardless of their recapitulation in individual claims or their back-reference.

The drawings show the following:

FIG. 1 schematically illustrates one preferred embodiment, and use by way of example, of the irradiation apparatus. The inner ear of the wearer 1 of the irradiation apparatus is prophylactically irradiated with near infrared light at location 2 via the photon emitter situated in the outer auditory canal. The measurement of the ambient noise level and the measurement of otoacoustic emissions likewise take place at location 2. The change in the bodily position of the wearer of the apparatus is measured using gyrometers 4 that are attached to the wearer at the hip. The measuring data may be wirelessly transmitted using Bluetooth technology 3.

FIG. 2 illustrates one preferred embodiment of the combination of the irradiation apparatus with a behind-the-ear hearing aid 8. Part A) shows the combination of the irradiation apparatus with the behind-the-ear hearing aid 8 in cross section, as used by a wearer of the apparatus. The sound-amplifying unit of the hearing aid together with light emitting diodes 6 are introduced into the outer auditory canal of the wearer of the apparatus. A silicone shield 5 is used for stabilization. Part B) shows a front view of the silicone shield with the light emitting diodes 6 fastened thereto. The light emitting diodes 6 are situated in a ring around the opening 7 through which the hearing aid provides the inner ear with sound.

FIG. 3 schematically illustrates one preferred embodiment of the combination of the irradiation apparatus with an in-the-ear hearing aid 9. Part C) shows the combination of the irradiation apparatus with the in-the-ear hearing aid 9 in cross section, as used by a wearer of the apparatus. The sound-amplifying unit of the hearing aid together with light emitting diodes 6 are introduced into the outer auditory canal of the wearer of the apparatus. A silicone shield 5 is used for stabilization. Part D) shows a front view of the silicone shield with the light emitting diodes 6 fastened thereto. The light emitting diodes 6 are situated in a ring around the opening 7 through which the hearing aid provides the inner ear with sound.

FIG. 4 illustrates one preferred embodiment and use of the irradiation apparatus. The hearing aid module of the irradiation apparatus comprises a device for measuring the reproducibility of distortion product otoacoustic emissions (DPOAE). In addition, the irradiation apparatus comprises a hip module comprising two gyroscopes with which a posturograph of the wearer of the irradiation apparatus is created. The risk of falling by the wearer of the irradiation apparatus is determined based on the data of the posturograph. The overall reproducibility, which is determined by the DPOAE measurement, as well as the risk of falling by the wearer of the irradiation apparatus are used to compute a base value of the power for the laser irradiation of the inner ear with near infrared light. In addition, the hearing aid module of the irradiation apparatus comprises a device for measuring the ambient noise level. Based on the value of the ambient noise level, the base power of the laser is modulated in such a way that near infrared irradiation of the inner ear takes place with an optimal, protective effect.

In addition, the changes in the bodily position of the wearer are determined using the gyroscopes and compared to limiting values. These limiting values may be normalized to the age, gender, or activity, or may be individually adapted by the wearer. If the measured change in the bodily position, for example in the case of uncontrolled body sway, exceeds the limiting values, an acoustic, visual, galvanic, and/or vibrotactile warning signal is sent to the wearer of the apparatus.

Figure 5:
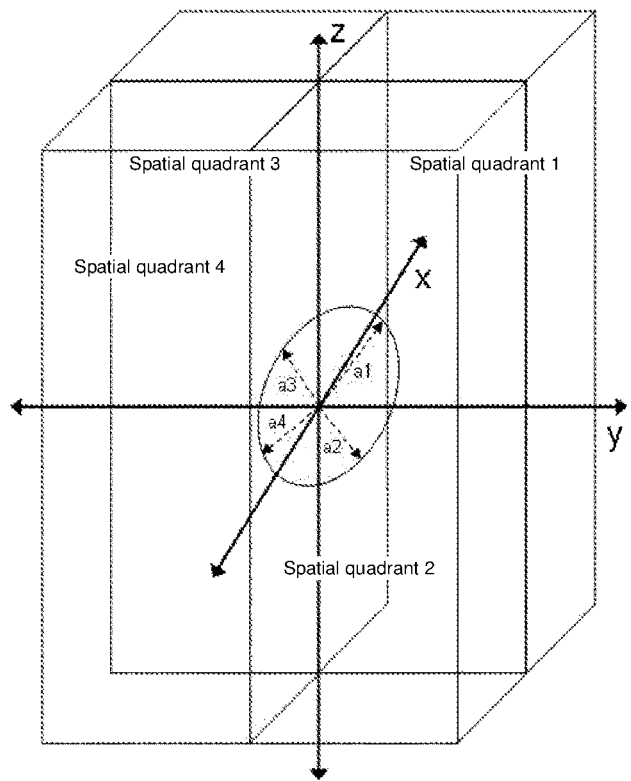
FIG. 5 shows a schematic illustration of the displacement vectors.

FIG. 5 illustrates the maximum displacement vectors in each spatial quadrant of the Cartesian coordinate system as dashed-line arrows (a1 to a4) for a change in the bodily position in space by way of example. An ellipse is spanned by the maximum displacement vectors for the movement.

Figure 6:
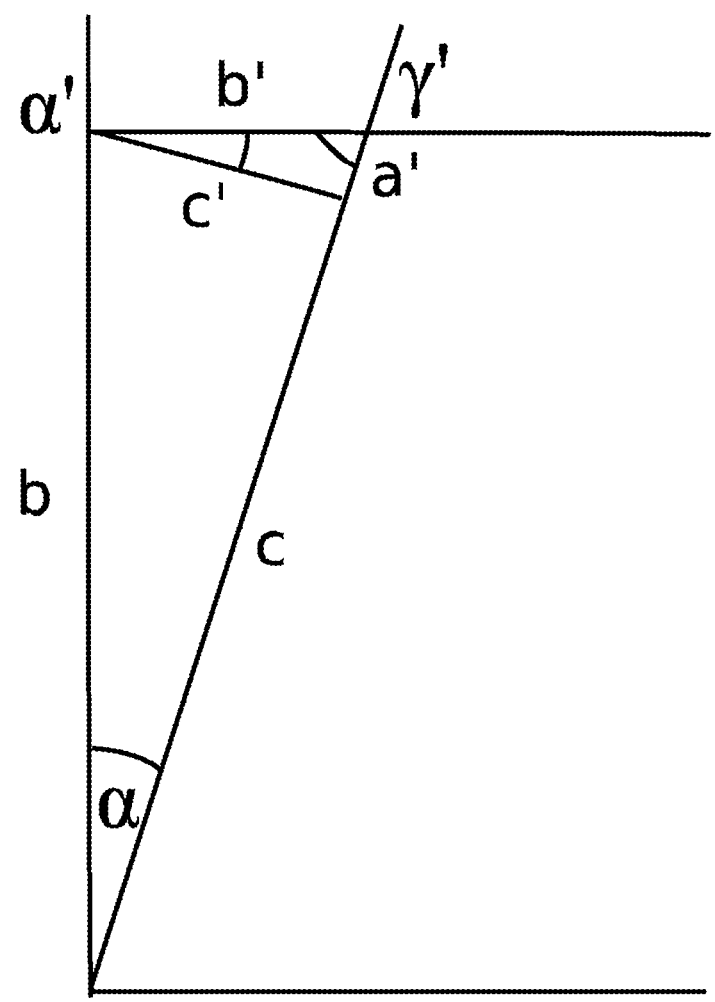
FIG. 6 shows a diagram for the computation of the angular velocity in the z axis.

FIG. 6 illustrates a schematic diagram by means of which the angular velocity in the z axis ($\alpha'$) is computed based on the determined values along the x or y reference axis.

EXAMPLES

The invention is explained in greater detail below with reference to examples, without being limited thereto.

In studies, patients with peripherally related hearing impairment and vertigo were provided with the irradiation apparatus according to the invention in order to counteract the further reduction in their hearing and equilibrium functions. To this end, a light emitting diode situated in the auditory canal irradiated light having a wavelength of 808 nm and a base irradiation power in the direction of the sensory hair cells present in the hearing and equilibrium organ. The irradiation was carried out on the patients at a base power for as long as the patients were not exposed to a harmful ambient noise level. The ambient noise level was continuously measured using a microphone. An ambient noise level of less than 85 dB was classified as a nonharmful ambient noise level. The level of the base irradiation power was determined monthly based on the extent of hair cells still present. For this purpose, the device carried out the measurement of the otoacoustic emissions as known in the prior art. When a decrease in the hair cell response, the reproducibility, was determined, the device increased the base irradiation power of the irradiation as a function of the hair cell loss. Reproducibility of greater than 60% was determined for the affected patients. PA was therefore 1 mW. In addition, the base power was determined for patients using a standardized balance test as the SBDT (see above). The SBDT score was less than 50% for the affected patients, and therefore the base irradiation power was not increased, and instead PC was 0 mW. The base irradiation power was thus 1 mW for the patients.

The patients spent most of the day with a nonharmful ambient noise level. The ambient noise level was continuously measured using a microphone. However, if the ambient noise level in certain situations exceeded 85 dB, the intensity of the irradiation was doubled for each further increase by 3 dB. The results show that this pretreatment reduces the temporary hearing loss by approximately 40 dB after working with very loud motors (105 dB) for 3 hours without protection, and thus protects the function of the inner ear to a significant degree.

Furthermore, in addition to the photon irradiation, patients received brief vibrotactile stimulation at the hip in the direction in which they swayed excessively. If the patients temporarily exhibited more than twice the age- and gender-related sway, a brief, intense vibrotactile or acoustic warning message was triggered. In order to reserve the warning message for fall prevention, the threshold for triggering the warning message was adapted by the patients to their typical everyday swaying movements by rejecting the warning message in situations not involving a falling risk. This individualization takes place in the device by learning new maximum possible swaying movements for which the patient does not require a warning message.

Figure 1:
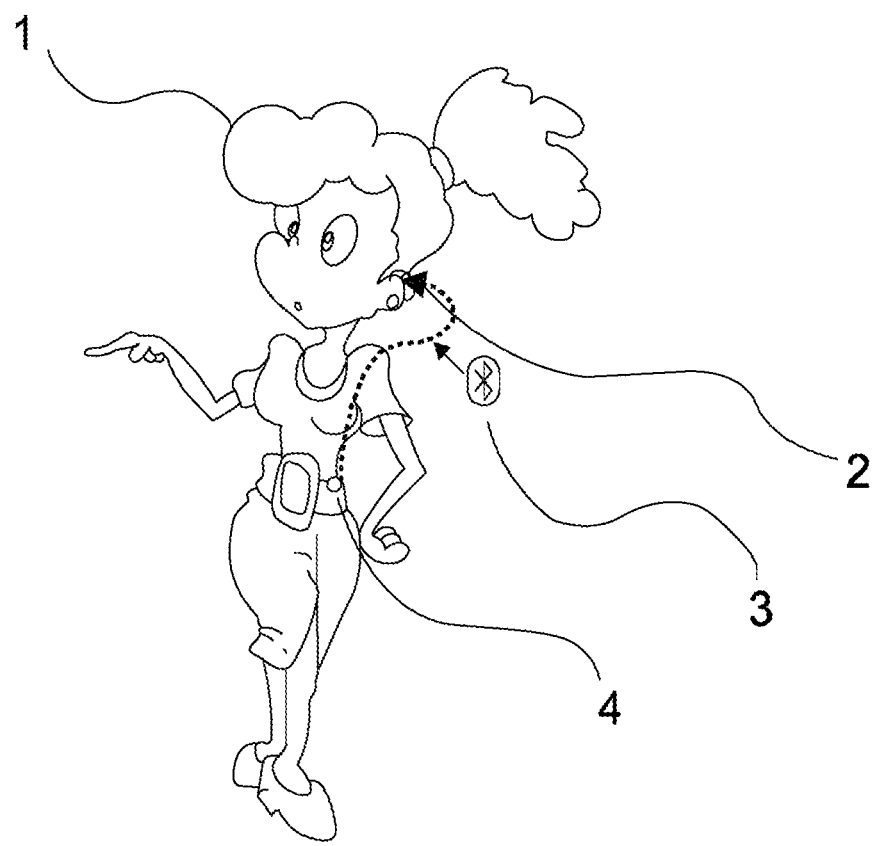
FIG. 1 shows a schematic illustration of one embodiment of the irradiation apparatus and use thereof by way of example.
Figure 2:
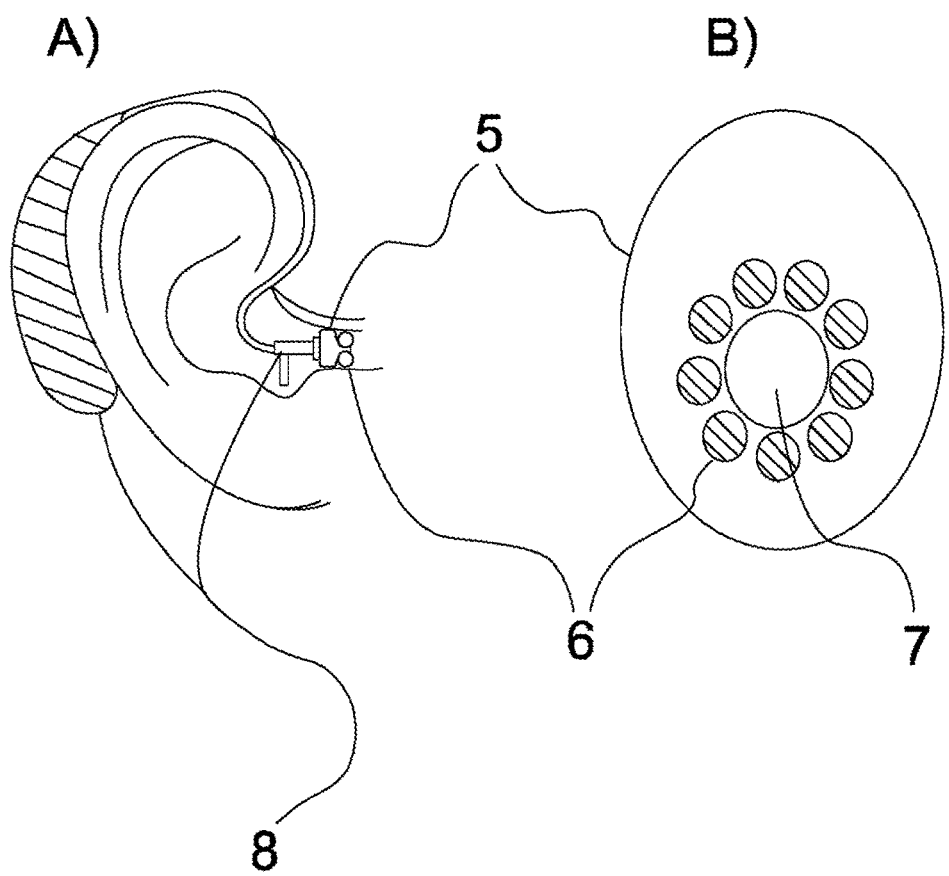
FIG. 2 shows a combination of the irradiation apparatus with a behind-the-ear hearing aid.
Figure 3:
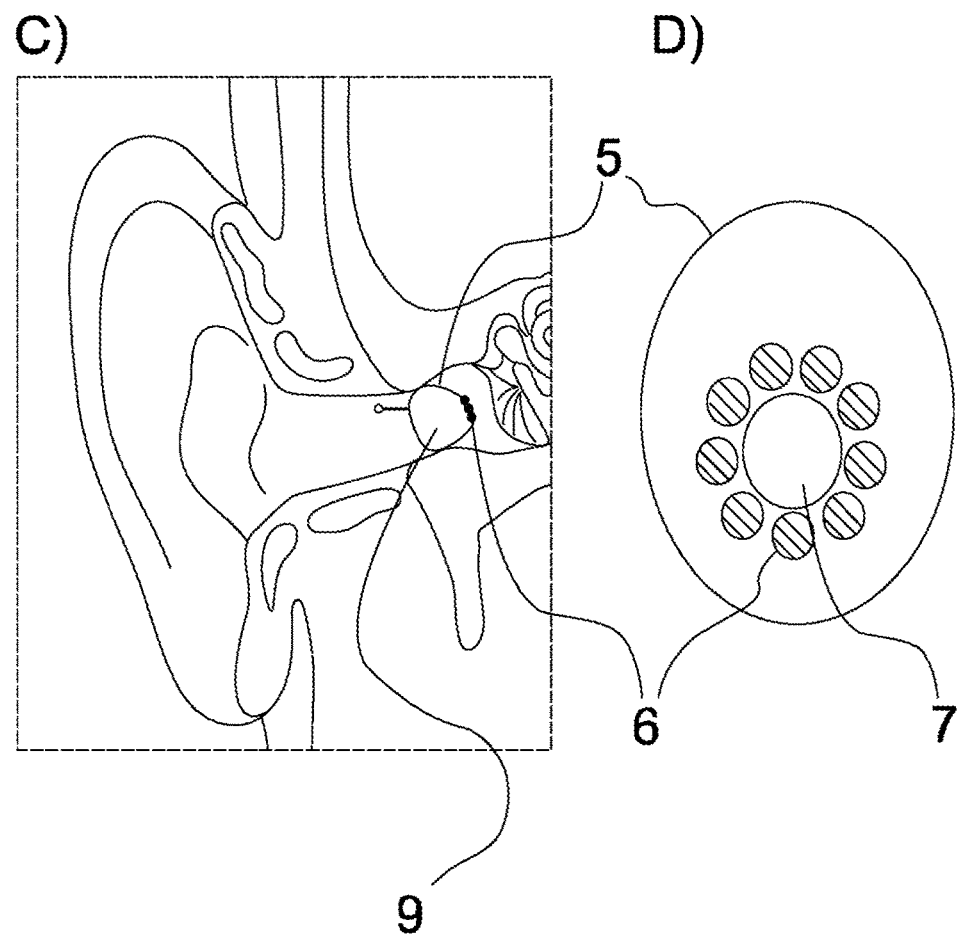
FIG. 3 shows a combination of the irradiation apparatus with an in-the-ear hearing aid.
Figure 4:
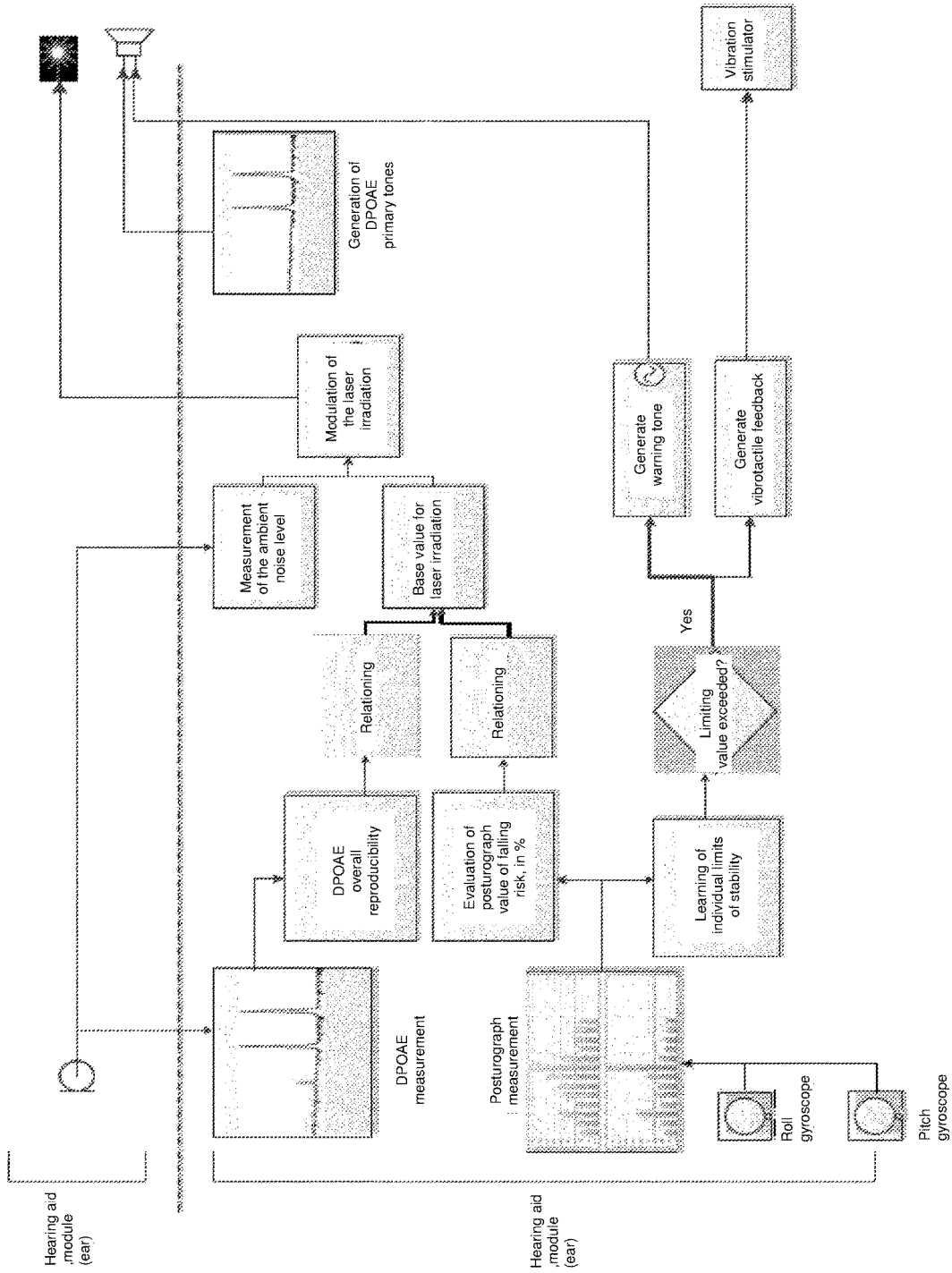
FIG. 4 shows a block diagram of use of the irradiation apparatus by way of example, with control of the power of the photon irradiation.

In the patients, the device module for measuring the change in the bodily position at the hip was in continuous wireless contact with the device module for photon irradiation on or in the ear via a Bluetooth module (FIG. 1) in order to convert the results of the determination of the equilibrium function for the photon irradiation. In some situations, patients perceived the wearing of both modules of the device to be uncomfortable. In these cases, the patients used only the module for the photon irradiation in the auditory canal (while at a concert, for example), or used only the module on the hip (while hiking, for example). This was made possible by the fact that both modules are usable independently of one another.

It should be noted that various alternatives to the described embodiments of the invention may be used in order to carry out the invention and arrive at the object according to the invention. Therefore, the embodiments of the apparatus according to the invention, of the method according to the invention, and of the system according to the invention are not limited to the preferred embodiments above. Rather, numerous embodiment variants that may differ from the approach described are possible. The objective of the claims is to define the scope of protection of the invention. The scope of protection of the claims is directed toward covering the apparatus, the method, and the system according to the invention and equivalent embodiments thereof.

TABLE 1

Standard values in °/s for 4 maximum spatial displacement vectors a1-a4 in the form a = (x, y, z) for specific movement sequences Age group: 20-30
Task:

| | | | | |
|---|---|---|---|---|
| Standing | a1 = (0.69, 1.36, −0.68) | a2 = (−1.73, 1.36, −0.86) | a3 = (0.69, −1.85, −0.93) | a4 = (−1.73, −1.85, −0.93) |
| Standing in the dark | a1 = (0.81, 1.38, −0.69) | a2 = (−1.90, 1.38, −0.95) | a3 = (0.81, −2.29, −1.14) | a4 = (−1.90, −2.29, −1.14) |
| Standing on one leg | a1 = (3.35, 3.82, −1.91) | a2 = (−4.36, 3.82, −2.18) | a3 = (3.35, −4.92, −2.46) | a4 = (−4.36, −4.92, −2.46) |
| Standing on one leg in | a1 = (15.98, 22.54, −11.27) | a2 = (−16.16, 22.54, −11.27) | a3 = (15.98, −20.51, −10.26) | a4 = (−16.16, −20.51, −10.26) |

TABLE 1-continued

Standard values in °/s for 4 maximum spatial displacement vectors a1-a4 in the form a = (x, y, z) for specific movement sequences

| Task | a1 | a2 | a3 | a4 |
|---|---|---|---|---|
| the dark | | | | |
| Balancing | a1 = (13.46, 16.68, −8.34) | a2 = (−20.01, 16.68, −10.01) | a3 = (13.46, −25.55, −12.77) | a4 = (−20.01, −25.55, −12.77) |
| Standing on soft ground | a1 = (0.71, 1.83, −0.92) | a2 = (−2.46, 1.83, −1.23) | a3 = (0.71, −3.07, −1.53) | a4 = (−2.46, −3.07, −1.53) |
| Standing on soft ground in the dark | a1 = (0.94, 1.83, −0.91) | a2 = (−2.39, 1.83, −1.20) | a3 = (0.94, −2.69, −1.35) | a4 = (−2.39, −2, 69, −1.35) |
| Standing on one leg (soft ground) | a1 = (4.83, 5.95, −2.97) | a2 = (−5.94, 5.95, −2.97) | a3 = (4.83, −6.75, −3.38) | a4 = (−5.94, −6.75, −3.38) |
| Balancing on soft ground | a1 = (17.19, 24.20, −12.10) | a2 = (−25.17, 24.20, −12.59) | a3 = (17.19, −34.65, −17.32) | a4 = (−25.17, −34.65, −17.32) |
| Walking with a lateral head movement | a1 = (20.69, 27.20, −13.60) | a2 = (−25.04, 27.20, −13.60) | a3 = (20.69, −27.43, −13.71) | a4 = (−25.04, −27.43, −13.71) |
| Walking with a vertical head movement | a1 = (21.41, 27.13, −13.56) | a2 = (−26.20, 27.13, −13.56) | a3 = (21.41, −32.91, −16.45) | a4 = (−26.20, −32.91, −16.45) |
| Walking in the dark | a1 = (18.19, 25.36, −12.68) | a2 = (−26.82, 25.36, −13.41) | a3 = (18.19, −33.33, −16.66) | a4 = (−26.82, −33.33, −16.66) |
| Climbing stairs | a1 = (29.06, 33.86, −16.93) | a2 = (−32.96, 33.86, −16.93) | a3 = (29.06, −43.91, −21.95) | a4 = (−32.96, −43.91, −21.95) |
| Walking over obstacles | a1 = (37.81, 49.18, −24.59) | a2 = (−36.01, 49.18, −24.57) | a3 = (37.81, −49.13, −24.57) | a4 = (−36.01, −49.13, −24.57) |
| Walking | a1 = (21.23, 27.77, −13.88) | a2 = (−30.11, 27.77, −15.06) | a3 = (21.23, −33.94, −16.97) | a4 = (−30.11, −33.94, −16.97) |
| Sitting down | a1 = (30.77, 26, 80, −15.39) | a2 = (−41.64, 26.80, −20.82) | a3 = (30.77, −41.85, −20.93) | a4 = (−41.64, −41.85, −20.93) |
| Standing up | a1 = (53.49, 48.60, −26.75) | a2 = (−29.55, 48.60, −24.30) | a3 = (53.49, −24.24, −26.75) | a4 = (−29.55, −24.24, −14.78) |
| Age group: 31-40 Task: | | | | |
| Standing | a1 = (0.92, 1.28, −0.64) | a2 = (−1.75, 1.28, −0.88) | a3 = (0.92, −2.35, −1.17) | a4 = (−1.75, −2.35, −1.17) |
| Standing in the dark | a1 = (0.75, 1.14, −0.57) | a2 = (−1.54, 1.14, −0.77) | a3 = (0.75, −2.00, −1.00) | a4 = (−1.54, −2.00, −1.00) |
| Standing on one leg | a1 = (2.77, 2.95, −1.47) | a2 = (−4.16, 2.95, −2.08) | a3 = (2.77, −3.71, −1.86) | a4 = (−4.16, −3.71, −2.08) |
| Standing on one leg in the dark | a1 = (18.34, 20.18, −10.09) | a2 = (−17.27, 20.18, −10.09) | a3 = (18.34, −19.46, −9.73) | a4 = (−17.27, −19.46, −9.73) |
| Balancing | a1 = (15.30, 16.63, −8.31) | a2 = (−21.55, 16.63, −10.77) | a3 = (15.30, −25.66, −12.83) | a4 = (−21.55, −25.66, −12.83) |
| Standing on soft ground | a1 = (2.57, 3.15, −1.58) | a2 = (−3.62, 3.15, −1.81) | a3 = (2.57, −3.46, −1.73) | a4 = (−3.62, −3.46, −1.81) |
| Standing on soft ground in the dark | a1 = (0.94, 1.49, −0.75) | a2 = (−2.24, 1.49, −1.12) | a3 = (0.94, −3.25, −1.62) | a4 = (−2.24, −3.25, −1.62) |
| Standing on one leg (soft ground) | a1 = (8.86, 7.98, −4.43) | a2 = (−10.28, 7.98, −5.14) | a3 = (8.86, −8.01, −4.43) | a4 = (−10.28, −8.01, −5.14) |
| Balancing on soft ground | a1 = (18.30, 23.97, −11.99) | a2 = (−25.94, 23.97, −12.97) | a3 = (18.30, −32.33, −16.16) | a4 = (−25.94, −32.33, −16.16) |
| Walking with a lateral head movement | a1 = (21.60, 26.38, −13.19) | a2 = (−25.29, 26.38, −13.19) | a3 = (21.60, −32.72, −16.36) | a4 = (−25.29, −32.72, −16.36) |
| Walking with a vertical head movement | a1 = (21.88, 23.20, −11.60) | a2 = (−21.79, 23.20, −11.60) | a3 = (21.88, −28.50, −14.25) | a4 = (−21.79, −28.50, −14.25) |
| Walking in the dark | a1 = (16.03, 21.38, −10.69) | a2 = (−23.40, 21.38, −11.70) | a3 = (16.03, −28.18, −14.09) | a4 = (−23.40, −28.18, −14.09) |
| Climbing stairs | a1 = (24.62, 39.98, −19.99) | a2 = (−30.64, 39.98, −19.99) | a3 = (24.62, −41.38, −20.69) | a4 = (−30.64, −41.38, −20.69) |
| Walking over obstacles | a1 = (33.25, 55.01, −27.50) | a2 = (−32.23, 55.01, −27.67) | a3 = (33.25, −55.35, −27.67) | a4 = (−32.23, −55.35, −27.67) |
| Walking | a1 = (19.95, 25.43, −12.72) | a2 = (−27.39, 25.43, −13.70) | a3 = (19.95, −31.01, −15.51) | a4 = (−27.39, −31.01, −15.51) |
| Sitting down | a1 = (37.80, 35.72, −18.90) | a2 = (−40.22, 35.72, −20.11) | a3 = (37.80, −43.72, −21.86) | a4 = (−40.22, −43.72, −21.86) |
| Standing up | a1 = (50.08, 49.36, −25.04) | a2 = (−29.87, 49.36, −24.68) | a3 = (50.08, −31.24, −25.04) | a4 = (−29.87, −31.24, −15.62) |
| Age group: 41-50 Task: | | | | |
| Standing | a1 = (0.69, 1.08, −0.54) | a2 = (−1.78, 1.08, −0.89) | a3 = (0.69, −2.26, −1.13) | a4 = (−1.78, −2.26, −1.13) |
| Standing in the dark | a1 = (0.65, 1.02, −0.51) | a2 = (−1.88, 1.02, −0.94) | a3 = (0.65, −2.43, −1.22) | a4 = (−1.88, −2.43, −1.22) |
| Standing on one leg | a1 = (6.67, 7.64, −3.82) | a2 = (−7.12, 7.64, −3.82) | a3 = (6.67, −6.76, −3.38) | a4 = (−7.12, −6.76, −3.56) |
| Standing on one leg in the dark | a1 = (26.21, 31.79, −15.90) | a2 = (−25.62, 31.79, −15.90) | a3 = (26.21, −33.98, −16.99) | a4 = (−25.62, −33.98, −16.99) |
| Balancing | a1 = (14.75, 19.55, −9.77) | a2 = (−20.77, 19.55, −10.38) | a3 = (14.75, −32.58, −16.29) | a4 = (−20.77, −32.58, −16.29) |
| Standing on soft ground | a1 = (1.53, 2.09, −1.05) | a2 = (−2.94, 2.09, −1.47) | a3 = (1.53, −3.53, −1.77) | a4 = (−2.94, −3.53, −1.77) |
| Standing on soft ground in the dark | a1 = (1.24, 1.46, −0.73) | a2 = (−3.01, 1.46, −1.50) | a3 = (1.24, −3.65, −1.82) | a4 = (−3.01, −3.65, −1.82) |
| Standing on one leg (soft ground) | a1 = (11.88, 13.09, −6.55) | a2 = (−11.16, 13.09, −6.55) | a3 = (11.88, −13.13, −6.57) | a4 = (−11.16, −13.13, −6.57) |
| Balancing on soft ground | a1 = (20.97, 24.87, −12.43) | a2 = (−26.00, 24.87, −13.00) | a3 = (20.97, −36.75, −18.37) | a4 = (−26.00, −36.75, −18.37) |
| Walking with a lateral head movement | a1 = (18.87, 29.07, −14.53) | a2 = (−26.50, 29.07, −14.53) | a3 = (18.87, −30.44, −15.22) | a4 = (−26.50, −30.44, −15.22) |
| Walking with a vertical head movement | a1 = (17.83, 22.81, −11.41) | a2 = (−24.71, 22.81, −12.35) | a3 = (17.83, −29.32, −14.66) | a4 = (−24.71, −29.32, −14.66) |
| Walking in the dark | a1 = (16.21, 21.97, −10.98) | a2 = (−23.39, 21.97, −11.69) | a3 = (16.21, −29.72, −14.86) | a4 = (−23.39, −29.72, −14.86) |
| Climbing stairs | a1 = (23.21, 40.15, −20.07) | a2 = (−30.01, 40.15, −20.07) | a3 = (23.21, −46.22, −23.11) | a4 = (−30.01, −46.22, −23.11) |
| Walking over obstacles | a1 = (41.71, 52.30, −26.15) | a2 = (−35.03, 52.30, −26.73) | a3 = (41.71, −53.46, −26.73) | a4 = (−35.03, −53.46, −26.73) |
| Walking | a1 = (17.78, 26.08, −13.04) | a2 = (−27.76, 26.08, −13.88) | a3 = (17.78, −32.92, −16.46) | a4 = (−27.76, −32.92, −16.46) |
| Sitting down | a1 = (38.42, 31.36, −19.21) | a2 = (−46.14, 31.36, −23.07) | a3 = (38.42, −45.03, −22.51) | a4 = (−46.14, −45.03, −23.07) |
| Standing up | a1 = (54.58, 46.19, −27.29) | a2 = (−33.15, 46.19, −23.09) | a3 = (54.58, −28.31, −27.29) | a4 = (−33.15, −28.31, −16.58) |
| Age group: 51-60 Task: | | | | |
| Standing | a1 = (1.31, 1.18, −0.66) | a2 = (−1.82, 1.18, −0.91) | a3 = (1.31, −2.83, −1.42) | a4 = (−1.82, −2.83, −1.42) |
| Standing in the dark | a1 = (0.90, 1.10, −0.55) | a2 = (−1.83, 1.10, −0.92) | a3 = (0.90, −2.53, −1.26) | a4 = (−1.83, −2.53, −1.26) |
| Standing on one leg | a1 = (3.83, 5.00, −2.50) | a2 = (−4.28, 5.00, −2.50) | a3 = (3.83, −5.76, −2.88) | a4 = (−4.28, −5.76, −2.88) |
| Standing on one leg in the dark | a1 = (23.80, 35.06, −17.53) | a2 = (−24.60, 35.06, −17.53) | a3 = (23.80, −30.47, −15.23) | a4 = (−24.60, −30.47, −15.23) |
| Balancing | a1 = (15.06, 18.79, −9.39) | a2 = (−19.62, 18.79, −9.81) | a3 = (15.06, −27.10, −13.55) | a4 = (−19.62, −27.10, −13.55) |
| Standing on soft ground | a1 = (1.60, 1.58, −0.80) | a2 = (−3.23, 1.58, −1.61) | a3 = (1.60, −3.75, −1.87) | a4 = (−3.23, −3.75, −1.87) |

TABLE 1-continued

Standard values in °/s for 4 maximum spatial displacement vectors a1-a4 in the form a = (x, y, z) for specific movement sequences

| | | | | |
|---|---|---|---|---|
| Standing on soft ground in the dark | a1 = (1.56, 1.92, −0.96) | a2 = (−2.76, 1.92, −1.38) | a3 = (1.56, −3.34, −1.67) | a4 = (−2.76, −3.34, −1.67) |
| Standing on one leg (soft ground) | a1 = (15.44, 17.67, −8.83) | a2 = (−16.37, 17.67, −8.83) | a3 = (15.44, −16.27, −8.13) | a4 = (−16.37, −16.27, −8.18) |
| Balancing on soft ground | a1 = (24.61, 26.51, −13.25) | a2 = (−22.83, 26.51, −13.25) | a3 = (24.61, −29.69, −14.84) | a4 = (−22.83, −29.69, −14.84) |
| Walking with a lateral movement head | a1 = (22.53, 31.92, −15.96) | a2 = (−24.79, 31.92, −15.96) | a3 = (22.53, −31.95, −15.97) | a4 = (−24.79, −31.95, −15.97) |
| Walking with a vertical head movement | a1 = (16.52, 22.94, −11.47) | a2 = (−21.48, 22.94, −11.47) | a3 = (16.52, −24.11, −12.06) | a4 = (−21.48, −24.11, −12.06) |
| Walking in the dark | a1 = (16.14, 20.72, −10.36) | a2 = (−20.44, 20.72, −10.36) | a3 = (16.14, −23.97, −11.98) | a4 = (−20.44, −23.97, −11.98) |
| Climbing stairs | a1 = (26.53, 44.67, −22.34) | a2 = (−27.79, 44.67, −22.34) | a3 = (26.53, −39.80, −19.90) | a4 = (−27.79, −39.80, −19.90) |
| Walking over obstacles | a1 = (43.24, 71.09, −35.55) | a2 = (−34.88, 71.09, −35.55) | a3 = (43.24, −61.64, −30.82) | a4 = (−34.88, −61.64, −30.82) |
| Walking | a1 = (19.36, 28.46, −14.23) | a2 = (−25.80, 28.46, −14.23) | a3 = (19.36, −29.91, −14.95) | a4 = (−25.80, −29.91, −14.95) |
| Sitting down | a1 = (44.06, 42.20, −22.03) | a2 = (−40.96, 42.20, −21.10) | a3 = (44.06, −46.81, −23.41) | a4 = (−40.96, −46.81, −23.41) |
| Standing up | a1 = (51.90, 55.69, −27.84) | a2 = (−35.93, 55.69, −27.84) | a3 = (51.90, −38.22, −25.95) | a4 = (−35.93, −38.22, −19.11) |

The invention claimed is:

1. An irradiation apparatus for prophylaxis of hearing impairment and/or vertigo comprising:
a photon emitter having an output power configured for irradiating an inner ear at a wavelength between 600 nm and 1200 nm,
a device configured to measure acoustic signals of surroundings, wherein the device determines a sound pressure level, and
an automated control unit, wherein
the automated control unit is configured to control the output power of the photon emitter based on the measured sound pressure level in a range between 0.1 mW and 1000 mW, wherein the photon emitter is configured so that the output power is:
a constant function of the sound pressure level up to a sound pressure level limiting value, and
a monotonically increasing function from the sound pressure level limiting value.

2. The irradiation apparatus according to claim 1, wherein the wavelength is between 700 nm and 900 nm.

3. The irradiation apparatus according to claim 1, wherein the sound pressure level limiting value is between 75 dB and 95 dB.

4. The irradiation apparatus according to claim 1, wherein a sound level meter is provided configured to measure the sound pressure level in a preferred sound frequency range of 50 Hz to 20,000 Hz, and, optionally, determines weighting in dB (A).

5. The irradiation apparatus according to claim 4, wherein the preferred sound frequency range is 250 Hz to 8000 Hz.

6. The irradiation apparatus according to claim 1, wherein the apparatus comprises a device configured to measure evoked otoacoustic emissions of the inner ear, to transmit measured data to the control unit for controlling the output power of the photon emitter.

7. The irradiation apparatus according to claim 1, wherein the irradiation apparatus comprises a device configured to measure a change in a bodily position of a wearer of the irradiation apparatus, and to transmit measured data to the control unit for controlling the output power of the photon emitter.

8. The irradiation apparatus according to claim 7, wherein the device configured to measure the change in a bodily position of the wearer of the irradiation apparatus is further configured to determine in three-dimensional space as a change in angular velocity of forward, backward, and lateral movements of a center of gravity of the wearer's body.

9. The irradiation apparatus according to claim 7, wherein the device configured to measure the change in the bodily position of the wearer of the irradiation apparatus comprises multiple mutually orthogonal gyrometers that are configured to determine the change in the angular velocity of forward, backward, and lateral movements of the body.

10. The irradiation apparatus according to claim 1, wherein the irradiation apparatus comprises actuators that are adapted to be attached to a body of a wearer, wherein the actuators are configured so that an activity of the actuators is proportional to a determined change in a bodily position, and are also configured so that an activation does not occur within limits of values of change in the bodily position based on a movement sequence.

11. The irradiation apparatus according to claim 1, wherein the photon emitter is a laser diode comprising a semiconductor material selected from the group consisting of gallium arsenide (GaAs), aluminum gallium arsenide (AlGaAs), indium gallium arsenide (InGaAs), gallium arsenide phosphide (GaAsP), aluminum gallium indium phosphide (AlGaInP), and gallium phosphide (GaP); or
in that the photon emitter is a light emitting diode, preferably a light emitting diode comprising a semiconductor material selected from the group consisting of gallium arsenide (GaAs), aluminum gallium arsenide (AlGaAs), indium gallium arsenide (InGaAs), gallium arsenide phosphide (GaAsP), aluminum gallium indium phosphide (AlGaInP), gallium phosphide (GaP), gallium arsenide phosphide (GaAsP), aluminum gallium indium phosphide (AlGaInP), and gallium arsenide phosphide (GaP).

12. The irradiation apparatus according to claim 1, wherein the photon emitter is a laser.

13. The irradiation apparatus according to claim 1, wherein the output power is set between 0.5 mW and 300 mW.

14. The irradiation apparatus according to claim 1, wherein the output power is set between 1 mW and 120 mW.

15. The irradiation apparatus according to claim 1, wherein a photon beam of the photon emitter is conducted through a photon beam conduction system, wherein the photon beam conduction system comprises an optical fiber cable that has an outer diameter of 1 mm to 8 mm.

16. The irradiation apparatus according to claim 15, wherein the optical fiber cable has an outer diameter of 3 mm to 5 mm.

17. The irradiation apparatus according to claim 15, wherein the photon beam conduction system comprises lenses and/or mirrors that bundle, expand, and/or collimate the photon beam.

18. The irradiation apparatus according to claim 15, wherein the photon beam conduction system is configured to conduct the photon beam to a predetermined region of the inner ear, the predetermined region optionally comprising the cochlea and/or the vestibule.

19. The irradiation apparatus according to claim 1, wherein the irradiation apparatus is present in combination with a hearing aid, wherein the hearing aid is a sound-amplifying device.

20. The irradiation apparatus according to claim 19, wherein the hearing aid is an in-the-ear device or a behind-the-ear device.

21. The irradiation apparatus according to claim 19, wherein the hearing aid is an implantable hearing aid.

22. The irradiation apparatus according to claim 19, wherein the hearing aid is a cochlea implant.

23. A system for protective irradiation of an inner ear of a wearer for the prophylaxis of hearing impairment and/or vertigo, comprising an irradiation apparatus according to claim 1, wherein the system is configured to:
   a) measure signals concerning the wearer of the irradiation apparatus and/or surroundings of the wearer,
   b) calculate the output power (P) of the photon emitter for protective irradiation of the inner ear based on data measured in a),
   c) setting the output power of the photon emitter to a value of output power P calculated in b), and effecting the irradiation of the inner ear with the output power P,
   wherein the data measured in a) comprise acoustic signals from the wearer's surroundings and at least a parameter B for calculating the output power P of the photon radiation is determined based on said measured data, and the measured data comprise evoked otoacoustic emissions of the outer hair cells of the inner ear, and at least a parameter A for calculating the output power P of the photon radiation is determined from this measured data and/or the measured data comprise changes in the bodily position of the wearer of the irradiation apparatus, and at least a parameter C for calculating the output power P of the photon radiation is determined from this measured data,
   wherein the output power P is calculated from the sum of three positive summands,
   wherein the first summand PA is calculated using parameter A, the second summand PB is calculated using parameter B, and the third summand PC is calculated using parameter C, and if the sum of PA, PB, and PC exceeds a maximum value M, then P=M, wherein the maximum value is preferably between 100 mW and 300 mW, and most preferably is 120 mW.

24. The system according to claim 23, wherein parameter A, determined by measuring the evoked otoacoustic emissions, is reproducibility, and PA is a monotonically decreasing function of A, wherein preferably PA=1 mW for A>=59% and PA=(60%−A)*1 mW for A<59%.

25. The system according to claim 23, wherein parameter B is the sound pressure level and PB is a monotonically increasing function of B, PB is 0 mW for values of B that are below a sound pressure level limiting value (G), the sound pressure level limiting value G being between 75 dB and 95 dB, preferably at 85 dB, and preferably being calculated for B>=G PB by PB=$2^{floor((B-G)/3\ dB)+1}$*(PA+PC)−(PA+PC).

26. The system according to claim 23, wherein parameter C is determined in a balance test, and is calculated from the forward, backward, and/or lateral movements of the wearer of the irradiation apparatus, based on standard values that are specific to age, gender, and exercise, wherein C is preferably measured in %, and corresponds to the standard balance deficit test (SBDT) composite score, wherein preferably PC=0 mW for C less than 50%, and PC=(C−45%)*0.2 mW for C greater than or equal to 50%.

27. A method for the protective irradiation of an inner ear for prophylaxis of hearing impairment and/or vertigo, using an irradiation apparatus according to claim 1, comprising:
   a) measuring signals concerning a wearer of the irradiation apparatus and/or the surroundings of the wearer,
   b) computing, based on the measuring data in a), the output power (P) of the photon radiation for the protective irradiation of the inner ear,
   c) controlling the output power of the photon emitter to the computed value P and irradiating the inner ear with the output power (P).

28. The method according to claim 27, wherein the measured data comprise evoked otoacoustic emissions of the outer hair cells of the inner ear, and at least a first parameter A for calculating the output power (P) of the photon radiation is determined from these measured data.

29. The method according to claim 28, wherein the measured data comprise acoustic signals from the surroundings of the wearer, and at least a second parameter B for calculating the output power (P) of the photon radiation is determined from these measured data.

30. The method according to claim 29, wherein the measured data comprise changes in the bodily position of the wearer of the irradiation apparatus, and at least a third parameter C for calculating the output power (P) of the photon radiation is determined from these measured data.

31. The method according to claim 30, wherein the output power (P) is calculated from the sum of three positive summands, wherein a first summand PA is computed using parameter A, the second summand PB is calculated using parameter B, and the third summand PC is calculated using parameter C, and if the sum of PA, PB, and PC exceeds a maximum value M, then P=M.

32. The method according to claim 31, wherein the maximum value is preferably between 100 mW and 300 mW, or 120 mW.

33. The method according to claim 31, wherein parameter A, determined by measuring the evoked otoacoustic emissions, is a reproducibility, and PA is a monotonically decreasing function of A.

34. The method according to claim 33, wherein for A≥59%, PA=1 mW and for A<59%, PA=(60%−A)*1 mW.

35. The method according to claim 31, wherein parameter B is a sound pressure level, and PB is a monotonically increasing function of B.

36. The method according to claim 35, wherein PB is 0 mW for values of B that are below a sound pressure level limiting value (G).

37. The method according to claim 36, wherein the sound pressure level limiting value (G) is between 75 dB and 95 dB, and preferably is 85 dB.

38. The method according to claim 36, wherein for B≥G, PB is computed by $$PB=2^{floor((B-G)/3\ dB)+1}*(PA+PC)-(PA+PC).$$

39. The method according to claim 31, wherein parameter C is determined in a balance test, and is computed from the forward, backward, and/or lateral movements of the wearer of the irradiation apparatus, based on standard values that are specific to age, gender, and exercise, wherein C is preferably measured in %, and corresponds to the standard balance deficit test (SBDT) composite score.

40. The method according to claim 39, wherein for C less than 50%, PC=0 mW, and for C greater than or equal to 50%, PC=(C−45%)*0.2 mW.

\* \* \* \* \*